(12) United States Patent
Kim et al.

(10) Patent No.: US 9,555,091 B2
(45) Date of Patent: Jan. 31, 2017

(54) BACULOVIRUS-BASED VACCINES

(71) Applicants: Konkuk University Industrial Cooperation Corp., Seoul (KR); KR Biotech Co., Ltd., Seoul (KR)

(72) Inventors: Young-Bong Kim, Goyang-Si (KR); Hee Jung Lee, Seoul (KR); Nuri Park, Seoul (KR); Yu-Kyoung Oh, Seoul (KR)

(73) Assignees: KONKUK UNIVERSITY INDUSTRIAL COOPERATION CORP., Seoul (KR); KR BIOTECH CO., LTD., Seoul (KR)

( * ) Notice: Subject to any disclaimer, the term of this patent is extended or adjusted under 35 U.S.C. 154(b) by 0 days.

(21) Appl. No.: 14/447,341

(22) Filed: Jul. 30, 2014

(65) Prior Publication Data

US 2015/0030621 A1 Jan. 29, 2015

Related U.S. Application Data

(62) Division of application No. 12/812,053, filed as application No. PCT/KR2009/000136 on Jan. 9, 2009, now abandoned.

(30) Foreign Application Priority Data

Jan. 9, 2008 (KR) ........................ 10-2008-0002733

(51) Int. Cl.
- *C12N 15/866* (2006.01)
- *A61K 39/12* (2006.01)
- *C12N 15/86* (2006.01)
- *C12N 7/00* (2006.01)
- *A61K 39/00* (2006.01)

(52) U.S. Cl.
CPC .............. *A61K 39/12* (2013.01); *C12N 7/00* (2013.01); *C12N 15/86* (2013.01); *A61K 2039/5256* (2013.01); *C12N 2710/14143* (2013.01); *C12N 2710/14145* (2013.01); *C12N 2710/14171* (2013.01); *C12N 2710/20034* (2013.01); *C12N 2740/10022* (2013.01); *C12N 2800/22* (2013.01); *C12N 2810/6054* (2013.01); *C12N 2830/60* (2013.01); *C12N 2830/85* (2013.01)

(58) Field of Classification Search
CPC ................... C12N 15/866; C12N 2750/14143; C12N 2800/50; C12N 15/86; C12N 2760/16134; C12N 15/8286; A61K 39/12; A61K 39/21; C07K 16/1036
See application file for complete search history.

(56) References Cited

U.S. PATENT DOCUMENTS

| 5,169,784 A | 12/1992 | Summers et al. |
| 5,858,723 A | 1/1999 | Mueller-Lantzsch et al. |
| 7,169,585 B2 | 1/2007 | Frazer et al. |

FOREIGN PATENT DOCUMENTS

| EP | 0265785 A3 | 5/1988 |
| WO | WO-92/02548 A1 | 2/1992 |
| WO | WO-98/55640 A1 | 12/1998 |
| WO | WO-01/16171 A1 | 3/2001 |

OTHER PUBLICATIONS

Blond et al., "An envelope glycoprotein of the human endogenous retrovirus HERV-W is expressed in the human placenta and fuses cells expressing the type D mammalian retrovirus receptor," J Virol. 74(7):3321-9 (2000).
Griffiths et al., "Hybrid human immunodeficiency virus gag particles as an anitgen carrier system: Induction of cytotoxic T-cell and humoral responses by a gag:V3 fusion," J Virology. 67:3191-98 (1993).
Kost et al., "Recombinant baculoviruses as expression vectors for insect and mammalian cells," Curr Opin Biotechnol. 10(5):428-33 (1999).
Thomsen et al., "Expression of feline leukaemia virus gp85 and gag proteins and assembly into virus-like particles using the baculovirus expression vector system," J Gen Virol. 73(Pt 7):1819-24 (1992).
Tonjes et al., "Expression of human endogenous retrovirus type K envelope glycoprotein in insect and mammalian cells," J Virol. 71(4):2747-56 (1997).
Tönjes et al., "Characterization of human endogenous retrovirus type K virus-like particles generated from recombinant baculoviruses," Virology. 233(2):280-91 (1997).
Wang et al., "Construction and immunogenicity of pseudotype baculovirus expressing GP5 and M protein of porcine reproductive and respiratory syndrome virus," Vaccine. 25:8220-27 (2007).
Zheng et al., "Highly efficient and economical baculovirus expression system for preparing human papillomavirus type16 virus-like particle," Acta Biochim Biophys Sin (Shanghai). 36(8):548-52 (2004).
International Search Report from PCT/KR2009/000136, dated Aug. 11, 2009 (7 pages).

*Primary Examiner* — Bao Li
(74) *Attorney, Agent, or Firm* — Harness, Dickey & Pierce, P.L.C.

(57) ABSTRACT

The present invention relates to a recombinant baculovirus comprising: (a) a nucleotide sequence encoding a foreign virus envelope protein; (b) a first promoter operatively linked to the envelope-encoding nucleotide sequence; (c) a nucleotide sequence encoding an antigen protein; and (d) a second promoter operatively linked to the antigen-encoding nucleotide sequence; and a vaccine composition using the same. The recombinant baculovirus of the present invention has an excellent efficacy on both humoral and cellular immune responses against a specific antigen (e.g., HPV L1), enabling to function as a more efficient DNA vaccine.

10 Claims, 15 Drawing Sheets

(A) Gardasil  
AcHERVenv-hER1a16L1  
(B) AcHERVenv-hER1a18L1  
(C) PBS

BACULOVIRUS-BASED VACCINES

BACKGROUND OF THE INVENTION

Field of the Invention

The present invention relates to a recombinant (chimera) baculovirus and a vaccine composition thereof.

Description of the Related Art

HPV (human papillomavirus) is a causative factor in the development of cervical cancer which occupies approximately 12% of global women's cancer. Incidence frequency and mortality of cervical cancer is higher enough to be at a rate of one person per 2 min in the world (*Vaccine* 24: 5235-5244 (2006)). Presently, about 100 types of HPV have been identified. Of them, HPV type 16 and HPV type 18 classified as high risk group have been found in the tissue of cervical cancer at a ratio of not less than 70% (*Vaccine* 22: 3004-3007 (2004)).

To modulate cervical cancer, an effective vaccine development for HPV infection has been attempted. First of all, there is urgently demanded a vaccine development for preventing cervical cancer.

HPV L1 protein as VLPs (virus like particles) has inherent self-assembly potential, allowing to form external envelopes without viral genome. It has been reported that VLP contributes to sufficient induction of immune responses to produce a neutral antibody having higher titer (*Journal of Virology* 81 (24): 13927-13931 (2007); *Virology* 321: 205-216 (2004); *Journal of Medical Virology* 80: 841-846 (2008)).

For efficient gene delivery in vivo, gene delivery systems have been developed using numerous viral vectors. For the purpose of gene therapy, viral vectors such as retrovirus and adenovirus are utilized to deliver HPV16L1 gene to an animal host (*Science* 260 (5110): 926-932 (1993)). However, utility of these viruses cause several drawbacks including: (a) virus proliferation in a replication-dependent manner; (b) cytotoxicity; (c) induction of early immune responses; and (d) expression of undesired viral genes.

By contrast, a baculovirus transfer vector has important advantages as follows: (a) insertion of a foreign gene having a relatively large size; and (b) post-translation processing due to use of insect cells (higher eukaryotic cells). The latter advantage is very crucial in the senses that the biological and immunological activity of a recombinant protein expressed by using a baculovirus transfer vector are almost equivalent to those of original protein compared with protein produced in prokaryote, *E. coli*. In addition, baculovirus has been known to be a biologically safe virus because its replication is impossible in animal cells and it induces no cytotoxicity (*Virology* 125: 107-117 (1983); *Hum. Gene Ther.* 7: 1937-1945 (1996); *Proc. Natl. Acad. Sci. USA* 96: 127-132 (1999); *Trends Biotechnol.* 20: 173-180 (2002)). It has been known that the replication of AcNPV (*Autographa californica* nuclear polyhedrosis virus) belonging to be an insect virus group is also impossible in a variety of animal cells, whereas it is possible to deliver a gene into cells through its infection (*Proc. Natl. Acad. Sci. USA* 92: 10099-10103 (1995); *Proc. Natl. Acad. Sci. USA* 93: 2348-2352 (1996)). Previously, it was reported that a specific gene in AcNPV genome could be highly expressed in animal cells where it is controlled by an animal promoter (*Journal of Virology*, 76 (11): 5729-5736 (2002); *Vaccine* 26 (20): 2451-2456 (2008)).

Recently, several studies tried to increase a gene transfer efficiency by introducing Env of other viruses onto the surface of baculovirus, for example including diverse reports obtaining higher gene transfer efficiency by introduction of a VSV envelope G protein onto the surface of baculovirus (*Journal of Virology*, 78 (16): 8663-8672 (2004); *Journal of Urology* 250 (2): 276-283 (2006); *Biochemical and Biophysical Research Communications* 289 (2): 444-450 (2001); *Journal of Virology* 75 (6): 2544-2556 (2001)), or by adding a gp64 protein on virus surface (*Human Gene Therapy*, 14 (1): 67-77 (2003)). In addition, vaccination using a baculovirus vector was known to induce immune responses against a hemagglutinin glycoprotein of influenza virus (*Journal of Immunology*, 171: 1133-1139 (2003)).

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventors have made intensive studies to develop a baculovirus-based vaccine capable of inducing more enhanced immune responses against various pathogens. As results, we have discovered that an expression construct and a recombinant baculovirus are prepared by combinations of a nucleotide sequence encoding an antigen gene and a nucleotide sequence encoding a foreign virus envelope protein, and immunization using the same leads to induce highly enhanced immune responses, providing a stable and economic vaccine.

Accordingly, it is an object of this invention to provide a recombinant baculovirus.

It is another object of this invention to provide a vaccine composition.

It is still another object to this invention to provide a method for inducing an immune response against a specific antigen.

It is further still another object to this invention to provide a nucleic acid molecule encoding a HERV (human endogenous retrovirus) envelope protein.

It is another object to this invention to provide a recombinant vector comprising a HERV envelope protein-encoding nucleic acid molecule.

It is still another object to this invention to provide a baculovirus-based gene delivery system comprising a HERV envelope protein-encoding nucleic acid molecule.

Other objects and advantages of the present invention will become apparent from the following detailed description together with the appended claims and drawings.

In one aspect of this invention, there is provided a recombinant baculovirus comprising: (a) a nucleotide sequence encoding a foreign virus envelope protein; (b) a first promoter operatively linked to the envelope-encoding nucleotide sequence; (c) a nucleotide sequence encoding an antigen protein; and (d) a second promoter operatively linked to the antigen-encoding nucleotide sequence.

In another aspect of this invention, there is provided a vaccine composition comprising the recombinant baculovirus of this invention as an active ingredient.

In still another aspect of this invention, there is provided a method for inducing an immune response against a specific antigen in a subject, comprising administering the vaccine composition of this invention.

The present inventors have made intensive studies to develop a baculovirus-based vaccine capable of inducing more enhanced immune responses against various pathogens. As results, we have discovered that an expression construct and a recombinant baculovirus are prepared by combinations of a nucleotide sequence encoding an antigen gene and a nucleotide sequence encoding a foreign virus envelope protein, and immunization using the same leads to induce highly enhanced immune responses, providing a stable and economic vaccine.

It is the most features of the present invention to utilize combinations of a nucleotide sequence encoding an antigen gene and a nucleotide sequence encoding a foreign virus [most preferably, HERV (human endogenous retrovirus)] envelope protein.

The recombinant baculovirus of this invention may be useful for delivery of various antigen genes. The term "antigen gene" or "nucleotide sequence encoding an antigen protein" used herein refers to a nucleotide sequence encoding an antigenic protein (for example, cell or virus envelope protein as an antigen) to be recognized by an immune system.

According to a preferable embodiment, the antigen includes a viral antigen, a bacterial antigen, a parasitic antigen or a cancer antigen, more preferably a viral antigen or a cancer antigen, and most preferably a viral antigen.

Illustrative example of the viral antigen capable of being used in the present invention includes an antigen derived from orthomyxoviruses such as influenza virus; retroviruses such as RSV (respiratory syncytial virus), SIV (simian immunodeficiency virus) and HIV; herpesviruses such as EBV (Epstein-Barr Virus); CMV (cytomegalovirus) or HSV (herpes simplex virus); lentiviruses; rhabdoviruses such as rabies; picomoviruses such as poliovirus; rotavirus; and parvoviruses. As the viral antigen to be more concrete, the example of HPV antigen includes HPV L1, L2, E6 or E7 protein; the example of HIV antigen includes a T-cell and B-cell epitope such as nef, p24, gp120, gp41, tat, rev, pol, env and gp120 (Palker et al., *J. Immunol.*, 142: 3612-3619 (1989)). The example of HBV envelope antigen is disclosed in Wu et al., *Proc. Natl. Acad. Sci., USA,* 86: 4726-4730 (1989). The example of rotavirus antigen includes VP4 (Mackow et al., *Proc. Natl. Acad. Sci., USA,* 87: 518-522 (1990)) and VP7 (Green et al., *J. Virol.,* 62: 1819-1823 (1988); influenza virus antigen includes a hemagglutin (HA) and a nucleoprotein; HSV antigen includes a thymidine kinase (Whitley et al., In: New Generation Vaccines, pages 825-854); avian influenza virus antigen includes a hemagglutin; hog cholera virus antigen includes an envelope protein; foot-and-mouth disease virus antigen includes an envelope protein; and Newcastle disease virus antigen includes HN (hemagglutinin-neuraminidase) or F (fusion protein).

Exemplary example of the bacterial antigen capable of being used in the present invention includes an antigen derived from *Mycobacterium* spp., *Helicobacter pylori, Salmonella* spp., *Shigella* spp., *E. Coli, Rickettsia* spp., *Listeria* spp., *Legionella pneumoniae, Pseudomonas* spp., *Vibrio* spp. and *Borellia burgdorferi*. More concretely, illustrative example of the bacterial antigen capable of being used in the present invention includes form-1 antigen of *Shigella sonnei* (Formal et al., *Infect. Immun.*, 34: 746-750 (1981)); an O-antigen of *V. cholerae* (Forrest et al. *J. Infect. Dis.* 159: 145-146 (1989); a FA/I fimbrial antigen of *E. coli* (Yamamoto et al., *Infect. Immun.,* 50: 925-928 (1985)) and a non-toxic B-subunit of thermosensitive toxin (Klipstein et al., *Infect. Immun.,* 40: 888-893 (1983)); a pertactin of *Bordetella pertussis* (Roberts et al., *Vacc.,* 10: 43-48 (1992)); an adenylate cyclase-hemolysin of *B. pertussis* (Guiso et al., *Micro. Path.,* 11: 423-431 (1991)); and a tetanus toxin fragment C of *Clostridium tetani* (Fairweather et al., *Infect. Immun.,* 58: 1323-1326 (1990)).

Exemplified example of the parasitic antigen capable of being used in the present invention includes an antigen derived from *Plasmodium* spp., *Trypanosome* spp., *Giardia* spp., *Boophilus* spp., *Babesia* spp., *Entamoeba* spp., *Eimeria* spp., *Laishmahia* spp., *Schistosome* spp., *Brugia* spp., *Fascida* spp., *Dirofilaria* spp., *Wuchereria* spp., and *Onchocerea* spp. More concretely, the example of the parasitic antigen capable of being used in the present invention includes a circumsporozoite antigen of *Plasmodium* spp. such as a circumsporozoite antigen of *Plasmodium bergerii* and a circumsporozoite antigen of *P. falciparum* (Sadoff et al., *Sci.,* 240: 336-337 (1988)); a merozoite surface antigen of *Plasmodium* spp. (Spetzler et al., *Int. J. Pept Prot. Res.,* 43: 351-358 (1994)); a galactose-specific lectin of *Entamoeba histolytica* (Mann et al., *Proc. Natl. Acad. Sci.*, USA, 88: 3248-3252 (1991)); a gp63 of *Leishmania* spp. (Russell et al., *J. Immunol.,* 140: 1274-1278 (1988)); a paramyosin of *Brugia malayi* (Li et al., *Mol. Biochem. Parasitol.,* 49: 315-323 (1991)); and a triose-phosphate isomerase of *Schistosoma mansoni* (Shoemaker et al., *Proc. Natl. Acad. Sci. USA,* 89: 1842-1846 (1992)).

Illustrative example of the cancer antigen capable of being used in the present invention includes a prostate-specific antigen (Gattuso et al., *Human Pathol.,* 26: 123-126 (1995)), TAG-72 and CEA (carcinoembryonic antigen) (Guadagni et al., *Int. J. Biol. Markers,* 9: 53-60 (1994)), MAGE-1 and thyrosinase (Coulie et al., *J. Immunothera.,* 14: 104-109 (1993)), p53 (WO 94/02167), NY-ESO1 (cancer-testis antigen), AFP (α-feto protein) and a cancer antigen 125 (CA-125), or EPCA (Early Prostate Cancer Antigen).

According to more preferable embodiment, the antigen used in the present invention includes a virual antigen or cancer antigen, and most preferably viral antigen.

Where the antigen gene used in the present invention is a viral antigen, the antigen preferably includes HPV (human papillomavirus) antigen, HBV (hepatitis B virus) antigen, HCV (hepatitis C virus) antigen, HIV (human immunodeficiency virus) antigen, rotavirus antigen, influenza virus antigen, HSV (herpes simplex virus) antigen, avian influenza virus antigen, hog cholera virus antigen, foot-and-mouth disease virus antigen and Newcastle disease virus antigen.

More preferably, the antigen includes HPV antigen, much more preferably HPV L1, L2, E6 or E7 protein, and most preferably HPV L1 protein.

HPV L1 protein has an original property capable of forming in vivo or in vitro virus like particles (VLPs) by self-assembly. L1 protein is the most conserved protein of HPV proteins. According to a preferable embodiment, the L1 nucleotide sequence used in the present invention is a nucleotide sequence derived from HPV selected from the group consisting of HPV type 1, 2, 3a, 4, 5, 6b, 7, 8, 9, 10, 11a, 12, 13, 16 and 18, and more preferably HPV type 16 or 18. For example, the nucleotide sequence encoding a L1 protein is described in GenBank accession Nos. EU118173 (*J. Virol.* 67 (12): 6929-6936 (1993)), AY383628 and AY383629 (*Virology* 321 (2): 205-216 (2004)).

The nucleotide sequence encoding a foreign virus envelope protein used in this invention may be derived from various viruses except for baculovirus. Preferably, the envelope protein is derived from a virus which utilizes a human cell as a host cell, more preferably a virus which has a target receptor on the surface of a human cell, and most preferably a virus which is able to induce a receptor-mediated phagocytosis in a human cell.

According to a preferable embodiment, the nucleotide sequence encoding a virus envelope protein used in the present invention is derived from alphavirus, paramyxovirus, rhabdoviridae, myxovirus, coronavirus, retrovirus, filovirus or arenavirus, more preferably retrovirus, and most preferably human endogenous retrovirus (HERV). HERV is an endogenous virus in human body, most of which are incorporated in human genome at an inactivated state. The envelope protein is expressed on the surface of recombinant virus, inducing phagocytosis by interaction with a receptor of a human cell.

According to a preferable embodiment, the nucleotide sequence encoding a HERV envelope protein is a nucleotide sequence encoding the amino acid sequence of SEQ ID NO:2, and more preferably a nucleotide sequence encoding SEQ ID NO:1. The nucleotide sequence of SEQ ID NO:1 may be optimized to highly express a HERV envelope protein in insect cells.

The chimera virus of the present invention is based on baculovirus. Baculovirus is a rod-shape virus, and its genes are not expressed in human cells using an insect-specific promoter. Therefore, baculovirus has been gradually spotlighted as a basic system of gene therapeutics in the senses that baculovirus induces no immune responses in human cells by viral gene expression. However, the expression of a foreign gene in a baculovirus vector is sharply induced under the control of a mammalian promoter. In addition, it is an advantage that the infection by baculovirus accelerates no replication of human endogenous virus. In contrast with other viruses for gene therapy, baculovirus may be cultured in serum-free media, contributing to massive production.

The construction of recombinant baculovirus and culture of insect cells are described in Summers and Smith. 1986. *A Manual of Methods for Baculovirus Vectors and Insect Culture Procedures*, Texas Agricultural Experimental Station Bull. No. 7555, College Station, Tex.; Luckow. 1991. In Prokop et al., *Cloning and Expression of Heterologous Genes in Insect Cells with Baculovirus Vectors' Recombinant DNA Technology and Applications,* 97-152; U.S. Pat. No. 4,745,051; and EP0340359 in detail, which are herein incorporated by references.

For instance, the chimera baculovirus containing a HERV Env gene and a HPV L1 gene allows a transfer vector delivering a HERV Env gene and a HPV L1 gene to transfect a cell. The expression construct containing a HERV Env gene and a HPV L1 gene is flanked with transposon sequence (e.g., Tn7). The transfer vector is transfected into a cell (e.g., *E. coli*) containing a bacmid (baculovirus shttle vector) with a mini-attTn7 target site and a helper plasmid with a transposase gene. Transfection of the transfer vector to *E. coli* may induce transposition, resulting in a recombinant bacmid. Subsequently, the recombinant bacmid is isolated and transfected into suitable insect cells, producing a chimera baculovirus. The insect cells suitable in the present invention are not particularly limited, for example including Sf9 (*Spodoptera frugiperda*), *Spodoptera exiaua, Choristoneura fumiferana, Trichoplusia ni* and *Spodoptera littoralis*, and *Drosophila.*

It is preferable that the nucleotide sequence encoding a virus envelope protein and HPV L1 in the recombinant baculovirus of the present invention is involved in a suitable expression construct. Preferably, the nucleotide sequence encoding a virus envelope protein and HPV L1 is operatively linked to a promoter in the expression construct. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. In the present invention, the promoter linked to the nucleotide sequence encoding a virus envelope protein and HPV L1 protein may be utilized in various manners.

According to a preferable embodiment, the first promoter operatively linked to the envelope-encoding nucleotide sequence is a promoter operable in insect cells, more preferably baculovirus IE-1 promoter, IE-2 promoter, p35 promoter, p10 promoter, gp64 promoter or polyhedrin promoter, and most preferably polyhedrin promoter.

According to a preferable embodiment, the second promoter operatively linked to the HPV L1-encoding nucleotide sequence is a promoter derived from a genome of a mammalian cell, or a promoter derived from a mammalian virus, more preferably U6 promoter, H1 promoter, CMV (cytomegalo virus) promoter, adenovirus late promoter, vaccinia virus 7.5K promoter, SV40 promoter, HSV tk promoter, RSV promoter, human elongation factor 1α (hEF1α) promoter, methallothionein promoter, β-actin promoter, human IL-2 gene promoter, human IFN gene promoter, human IL-4 gene promoter, human lymphotoxin gene promoter, human GM-CSF gene promoter, TERT promoter, PSA promoter, PSMA promoter, CEA promoter, E2F promoter, AFP promoter or albumin promoter, and most preferably hEF1α promoter.

Preferably, the expression construct used in the present invention includes a polyadenylation sequence, for example including hEF1α polyA, bovine hormone terminator (Gimmi, E. R., et al., *Nucleic Acids Res.* 17: 6983-6998 (1989)), SV40-derived polyadenylation sequence (Schek, N, et al., *Mol. Cell Biol.* 12: 5386-5393 (1992)), HIV-1 polyA (Klasens, B. I. F., et al., *Nucleic Acids Res.* 26: 1870-1876 (1998)), β-globin polyA (Gil, A., et al., *Cell* 49: 399-406 (1987)), HSV TK polyA (Cole, C. N. and T. P. Stacy, *Mol. Cell. Biol.* 5: 2104-2113 (1985)) or poliomavirus polyA (Batt, D. B and G. G. Carmichael, *Mol. Cell. Biol.* 15:4783-4790(1995)), but not limited to.

In the recombinant virus of the present invention, each envelope-encoding nucleotide sequence and HPV L1-encoding nucleotide sequence may be contained in an expression construct of a first promoter-envelope-encoding nucleotide sequence-polyA sequence and a second promoter-HPV L1-encoding nucleotide sequence-polyA sequence. In addition, envelope- and HPV L1-encoding nucleotide sequence may be involved as an expression construct of a first promoter-envelope-encoding nucleotide sequence-second promoter-HPV L1-encoding nucleotide sequence-polyA sequence.

According to a preferable embodiment, the recombinant virus of this invention further includes a gene of interest to be expressed. The gene of interest to be expressed by the recombinant virus of this invention is not particularly limited. The gene of interest in the present invention may be any gene, for example, including cancer-therapeutic genes encoding proteins having anti-tumor activity and eventually degenerating tumor cells such as tumor suppressor genes, immunomodulatory genes [e.g., cytokine genes, chemokine genes and costimulatory factor genes (for T cell activity such as B7.1 and B7.2)], suicide genes, cytotoxic genes, cytostatic genes, pro-apoptotic genes and anti-angiogenic genes, but not limited to.

The suicide genes encode proteins capable of conferring to tumor cells sensitivity to chemotherapeutic agents, or of inducing toxic conditions in tumor cells. The most well-known suicide gene is the thymidine kinase (TK) gene (U.S.

Pat. Nos. 5,631,236 and 5,601,818). Cells expressing TK are susceptible to selective cell death by gancyclovir. The tumor suppressor genes encode polypeptides to inhibit tumorigenesis. The tumor suppressor genes are inherent in mammalian cells and their deletion or inactivation is believed to be a prerequisite for tumorigenesis. Examples of the tumor suppressor genes include members of the tumor suppressor gene INK4 family, which are exemplified by APC, DPC4, NF-1, NF-2, MTS1, WT1, BRCA1, BRCA2, VHL, p53, Rb, MMAC-1, MMSC-2, retinoblastoma gene (Lee et al., Nature, 329: 642 (1987)), gene of adenomatous polyposis coli protein (U.S. Pat. No. 5,783,666), nasopharyngeal carcinoma tumor suppressor gene that maps at chromosome 3p21.3 (Cheng et al., Proc. Natl. Acad. Sci., 95: 3042-3047 (1998)), deleted in colon carcinoma (DCC) gene, MTS1, CDK4, VHL, p100Rb, p16 and p21, and therapeutically effective fragments thereof (e.g., p56Rb, p94Rb). It will be understood that other known anti-tumor genes can be used by those of ordinary skill in the art.

The term "cytotoxic gene" as used herein, refers to a nucleotide sequence, the expression of which in a cell elicits a toxic effect. Examples of the cytotoxic genes include nucleotide sequences encoding Pseudomonas exotoxin, ricin toxin, diphtheria toxin, and the like.

The term "cytostatic gene" as used herein, refers to a nucleotide sequence, the expression of which in a cell induces an arrest in the cell cycle. Examples of the cytostatic genes include, but are not limited to, p21, retinoblastoma gene, E2F-Rb fusion protein gene, genes encoding cyclin-dependent kinase inhibitors such as pI6, pI5, pI8 and pI9, growth arrest specific homeobox (GAX) gene (WO 97/16459 and WO 96/30385), and so forth.

In addition, a variety of therapeutic genes useful in treating various diseases may be carried in the gene delivery system of this invention. Non-limiting examples of the therapeutic genes include genes encoding cytokines (e.g., interferon-α, interferon-β, interferon-δ and interferon-γ), interleukins (e.g., IL-1, IL-2, IL-4, IL-6, IL-7, IL-10, IL-12, IL-19 and IL-20), colony-stimulating factors (e.g., GM-CSF and G-CSF), or chemokine genes [monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), eotaxin, 1-309, human protein HCC-1/NCC-2, human protein HCC-3, and mouse protein C10]. In addition, the therapeutic genes include genes encoding tissue-type plasminogen activator (tPA) or urokinase-type plasminogen activator, and LAL-generating gene to provide sustained thrombolysis for preventing hypercholesterolemia. Further, polynucleotide sequences available for treatment of various diseases including cystic fibrosis, adenosine deaminase deficiency, AIDS and other infectious diseases, and malignant and inflammatory diseases are known to be useful as therapeutic genes.

The term "pro-apoptotic gene" as used herein, refers to a nucleotide sequence, the expression of which results in the programmed cell death. Examples of the pro-apoptotic genes include p53, adenovirus E3-11.6K (derived from Ad2 and Ad5) or adenovirus E3-10.5K (derived from Ad), adenovirus E4 gene, Fas ligand, TNF-α, TRAIL, p53 pathway genes and genes encoding a series of caspases.

The term "anti-angiogenic gene" as used herein, refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (PNAS, 1998, 95, 8795-8800), endostatin, and so on.

The nucleotide sequences of interest described previously are available from DNA sequence databases such as Gen-Bank or EMBL.

The recombinant virus of the present invention may induce a receptor-mediated phagocytosis in a human cell by its envelope protein, and generate immune responses against an antigen protein in a body through injection of antigen protein to be expressed. Furthermore, the recombinant baculovirus of the present invention may remarkably induce cellular immune responses as well as humoral immune responses. Consequently, the recombinant baculovirus of the present invention may exhibit excellent efficacy on prevention of various disorders by functions as described above. As demonstrated in the following examples, the recombinant baculovirus of the present invention has not only almost similar effect on humoral immune responses compared with conventional vaccine, gardasil, but also excellent induction of cellular immunity against HPV, enabling to function as a HPV vaccine more efficient than gardasil.

The vaccine composition of the present invention includes: (a) a therapeutically effective amount of the recombinant baculovirus; and (b) a pharmaceutically acceptable carrier.

The recombinant baculovirus contained in the vaccine composition of the present invention exhibits immunogenicity against various antigens.

According to a preferable embodiment, the recombinant baculovirus contained in the vaccine composition of the present invention includes HPV antigen genes and the vaccine composition is a HPV vaccine composition.

The present composition may be used for prevention or treatment of various disorders (e.g., cervical cancer, rectal cancer, vulva cancer, penile cancer or head and neck cancer) caused by HPV infection, and preferably prevention. Most preferably, the present composition may be used for prevention or treatment of cervical cancer, and preferably prevention. The term "pharmaceutically effective amount" refers to an amount enough to show and accomplish efficacies and activities of the compound of this invention for preventing or treating, preferably preventing the mentioned-above disorders.

The pharmaceutically acceptable carrier contained in the vaccine composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propyl hydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative.

Preferably, the vaccine composition according to the present invention may be administered parenterally, e.g., by intravenous, intra-abdominal, intramuscular, transdermal or locally.

A suitable dosage amount of the vaccine composition of the present invention may vary depending on pharmaceutical formulation methods, administration methods, the patient's age, body weight, sex, pathogenic state, diet, administration time, administration route, an excretion rate and sensitivity for a used pharmaceutical composition. Generally, a skilled physician may determine and prescribe an effective dosage for treatment of interest in an easy manner. Preferably, the vaccine composition of the present invention may be administered with a daily dose of the recombinant viruses of $1 \times 10^3$-$1 \times 10^{15}$ pfu/ml.

According to the conventional techniques known to those skilled in the art, the vaccine composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

In another aspect of this invention, there is provided a recombinant baculovirus comprising: (a) a nucleotide sequence encoding a foreign virus envelope protein; (b) a first promoter operatively linked to the envelope-encoding nucleotide sequence; (c) a nucleotide sequence encoding a HPV (human papilloma virus) L1 protein; and (d) a second promoter operatively linked to the HPV L1-encoding nucleotide sequence.

Since the present recombinant baculovirus comprises the vaccine composition of this invention as active ingredients described above, the common descriptions between them are omitted in order to avoid undue redundancy leading to the complexity of this specification.

In still another aspect of this invention, there is provided a nucleic acid molecule encoding a HERV (human endogenous retrovirus) envelope protein, comprising a nucleotide sequence of SEQ ID NO:1.

The present inventors have made intensive studies to develop a more efficient gene delivery system based on baculovirus. As results, we have discovered that where an endogenous retrovirus is in a cell of interest and has no cytotoxity to the cell, the introduction of its envelope protein into a gene delivery system contributes to remarkable improvement of the gene delivery system's efficiency.

To develop an improved gene delivery system, we have optimized baculovirus expression in insect cells by modifying a nucleic acid molecule encoding a HERV envelope protein which is introduced into a gene delivery system.

The envelope gene introduced into the gene delivery system in the present invention is derived from HERV. HERV is incorporated into a human genome, and not expressed because it has incomplete genes as a whole. The present invention modifies a natural-occurring HERV envelope gene to express a non-expressed gene of HERV in insect cells in a high-throughput manner.

The term "nucleic acid" used herein, refers to a DNA molecule.

It could be understood that the HERV envelope-encoding nucleic acid 25 molecule of this invention includes substantially identical sequences to the sequences set forth in the appended Sequence Listing. The substantially identical sequences refers to those showing preferably at least 80%, more preferably at least 85%, still more preferably at least 90%, most preferably at least 95% nucleotide similarity to the sequences of the appended Sequence Listing, as measured using one of the sequence comparison algorithms known to those ordinarily skilled in the art, by which the nucleotide sequence of this invention is maximally aligned corresponding on random other nucleotide sequences. Methods of alignment of 5 sequences for comparison are well-known in the art. Various programs and alignment algorithms are described in: Smith and Waterman, Adv. Appl. Math. 2: 482 (1981); Needleman and Wunsch, J. Mol. Bio. 48: 443 (1970); Pearson and Lipman, Methods in Mol. Biol. 24: 307-31 (1988); Higgins and Sharp, Gene 73: 237-44 (1988); Higgins and Sharp, CABIOS 5: 151-3 (1989); Corpet et al., Nuc. Acids 10 Res. 16: 10881-90 (1988); Huang et at., Comp. Appl. BioSci. 8: 155-65 (1992); and Pearson et al., Meth. Mol. Biol. 24: 307-31 (1994). The NCBI Basic Local Alignment Search Tool (BLAST) (Altschul et al., J. Mol. Biol. 215: 403-10 (1990)) is available from several sources, including the National Center for Biological Information (NBCI, Bethesda, Md.) and on the Internet, for use in connection with the sequence 15 analysis programs blastp, blasm, blastx, tblastn and tblastx. It can be accessed at www.ncbi.nlm.nih.aov/BLAST/. A description of how to determine sequence identity using this program is available at www.ncbi.nlm.nih.gov/BIAST/blast help.html.

In another aspect of this invention, there is provided a recombinant vector comprising the nucleic acid molecule encoding a HERV envelope protein.

Since the present recombinant vector comprises the HERV envelope-encoding sequence described above, the common descriptions between them are omitted in order to avoid undue redundancy leading to the complexity of this specification.

The vector system of this invention may be performed by various methods known to those skilled in the art and its practical method is described in Sambrook et al, Molecular Cloning, A Laboratory Manual, Cold Spring Harbor Laboratory Press (2001), which is herein incorporated by reference.

In each a vector of this invention and an eukaryotic cell used as an expression vector and the host cell, the promoter derived from genome of mammalian cells, mammalian viruses or baculovirus (example: polyhedrin promoter) might be used, and polyadenylated sequence might be commonly used as the transcription termination sequence.

The expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

According to a preferable embodiment, the vector of the present invention has a gene map as shown in FIG. 11. The characteristics of the vector in FIG. 11 are as follows: (a) a HERV envelope gene expression is controlled by a polyhedrin promoter; (b) a gene expression of interest is modulated by a hEF1α promoter; (c) a hEF1α polyA signal as a transcription termination sequence; and (d) two arm of transposon 7 in both side of expression cassette.

In still another aspect of this invention, there is provided a baculovirus-based gene carrier comprising the nucleic acid molecule encoding a HERV envelope protein.

Since the present gene carrier is derived from viruses obtained by infecting the recombinant vector into insect cells described above, the common descriptions between them are omitted in order to avoid undue redundancy leading to the complexity of this specification.

Recently, the method using virus has been principally employed as a gene delivery system. Viruses used in the method include adenovirus, retrovirus, lentivirus, vaccinia and the like. Most of viruses have limitations for use in a human body because they has an opportunity to infect or danger a human, whereas baculovirus is known as a biologically stable virus as it has no infectivity to a human body and is able to be replicated only in specific insects. The virus-mediated gene delivery system is carried out through virus infection which is determined by interaction between a virus envelope protein and a receptor of a cell and an animal of interest.

Focusing on advantages of the baculovirus, the present invention provides a more improved gene delivery system whereby an envelope protein of endogenous virus present in an animal of interest is incorporated on the surface of baculovirus. The endogenous virus has been known to be widely distributed in all mammals such as pig, mouse, cat, dog, and so on.

According to the gene carrier of the present invention, the envelope protein of human endogenous virus is linked to its surface, enabling to deliver a gene of interest into a human cell in a high-throughput and stable manner. Therefore, the gene carrier of the present invention may be efficiently utilized for development of gene therapeutics against various disease and disorders.

The features and advantages of this invention are summarized as follows:

(a) The vaccine of the present invention includes a recombinant baculovirus containing a nucleotide sequence encoding an antigen gene and a foreign virus envelope protein.

(b) The recombinant baculovirus of the present invention may induce a receptor-mediated phagocytosis in a human cell by the envelope protein on the surface of baculovirus, and immune responses in the body injected with the antigen protein (e.g., HPV L1) to be expressed.

(c) Furthermore, the recombinant baculovirus of the present invention may significantly induce cellular immune responses as well as humoral immune responses.

(d) Ultimately, the recombinant baculovirus of the present invention may have an excellent efficacy on prevention of various diseases (e.g., cervical cancer) induced by a specific antigen as described above.

(e) The recombinant baculovirus of the present invention has not only almost similar effect on humoral immune responses compared with conventional vaccine, gardasil, but also excellent induction of cellular immunity against HPV, enabling to function as a HPV vaccine more efficient than gardasil.

(f) According to the present invention, a stable and economic vaccine may be provided.

BRIEF DESCRIPTION OF THE DRAWINGS

In FIG. 1, black arrow, white arrow, and small black quadrangle indicate polyhedrin promoter, hEF1α promoter, and hEF1α poly(A) signal, respectively.

In FIG. 2, black arrow, white arrow, and small black quadrangle indicate polyhedrin promoter, hEF1α promoter, and hEF1α poly(A) signal, respectively.

In FIG. 3, black arrow, white arrow, and small black quadrangle indicate polyhedrin promoter, hEF1α promoter, and hEF1α poly(A) signal, respectively.

Figure 4:
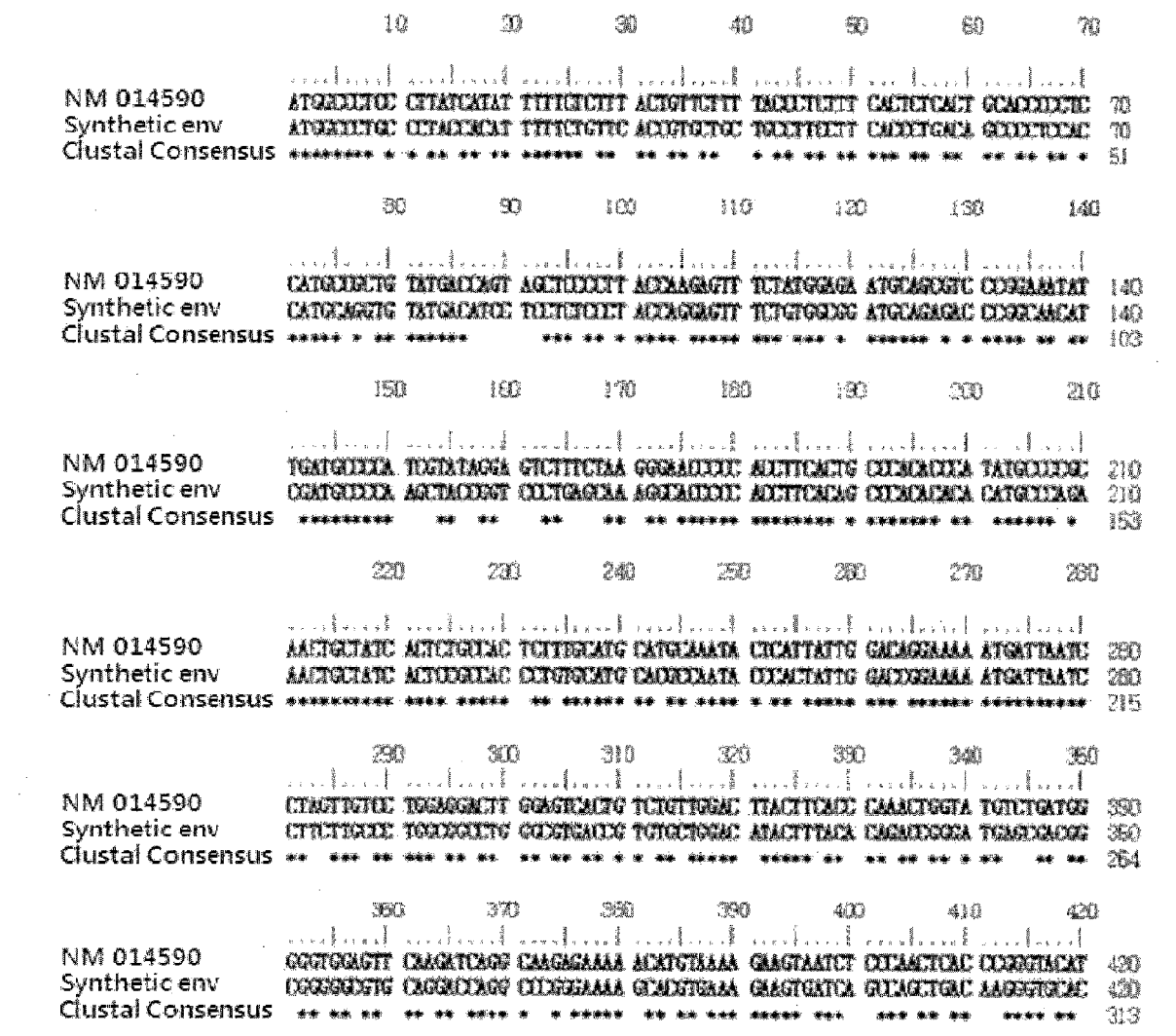
Figure 6:
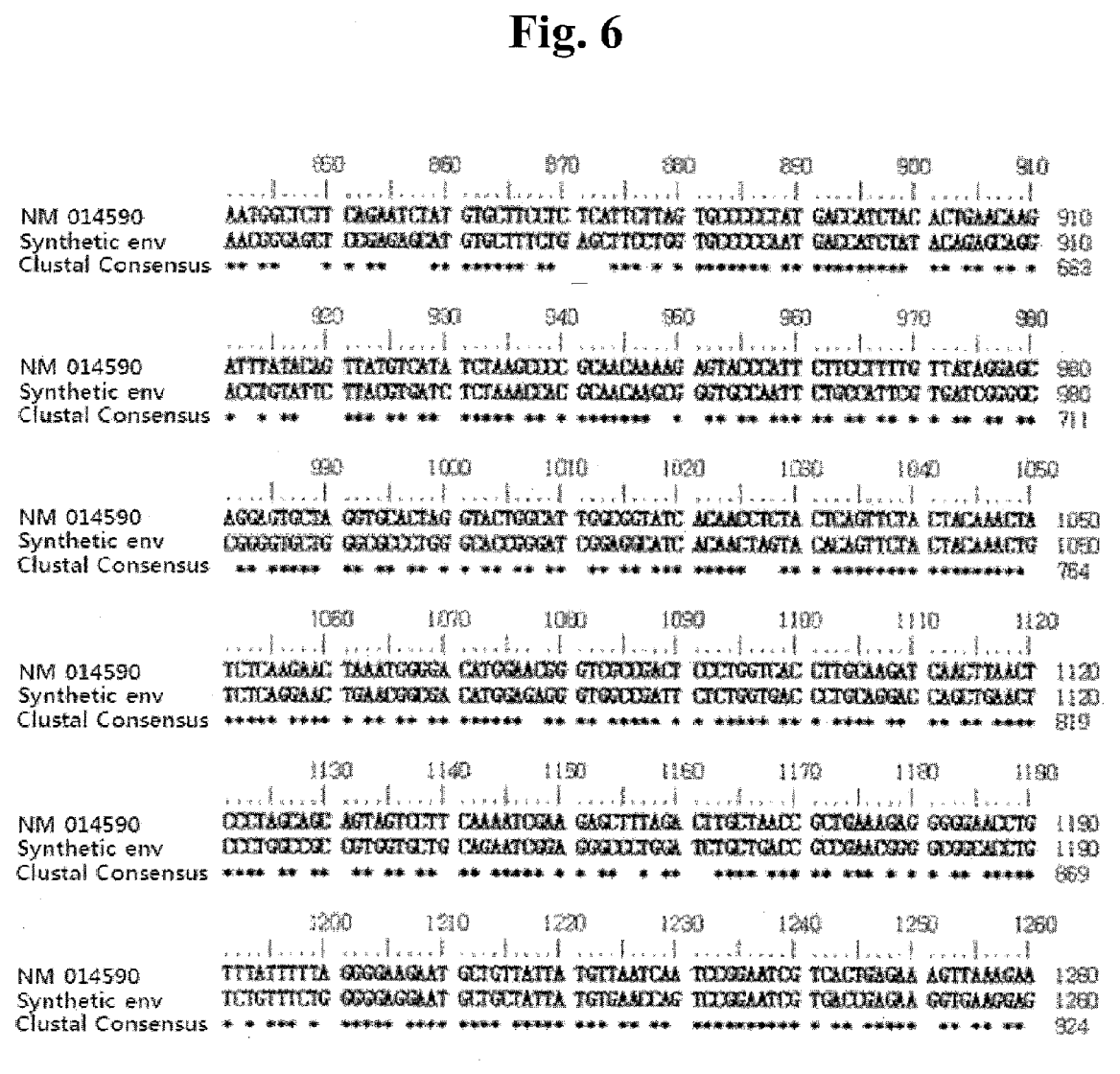
Figure 7:
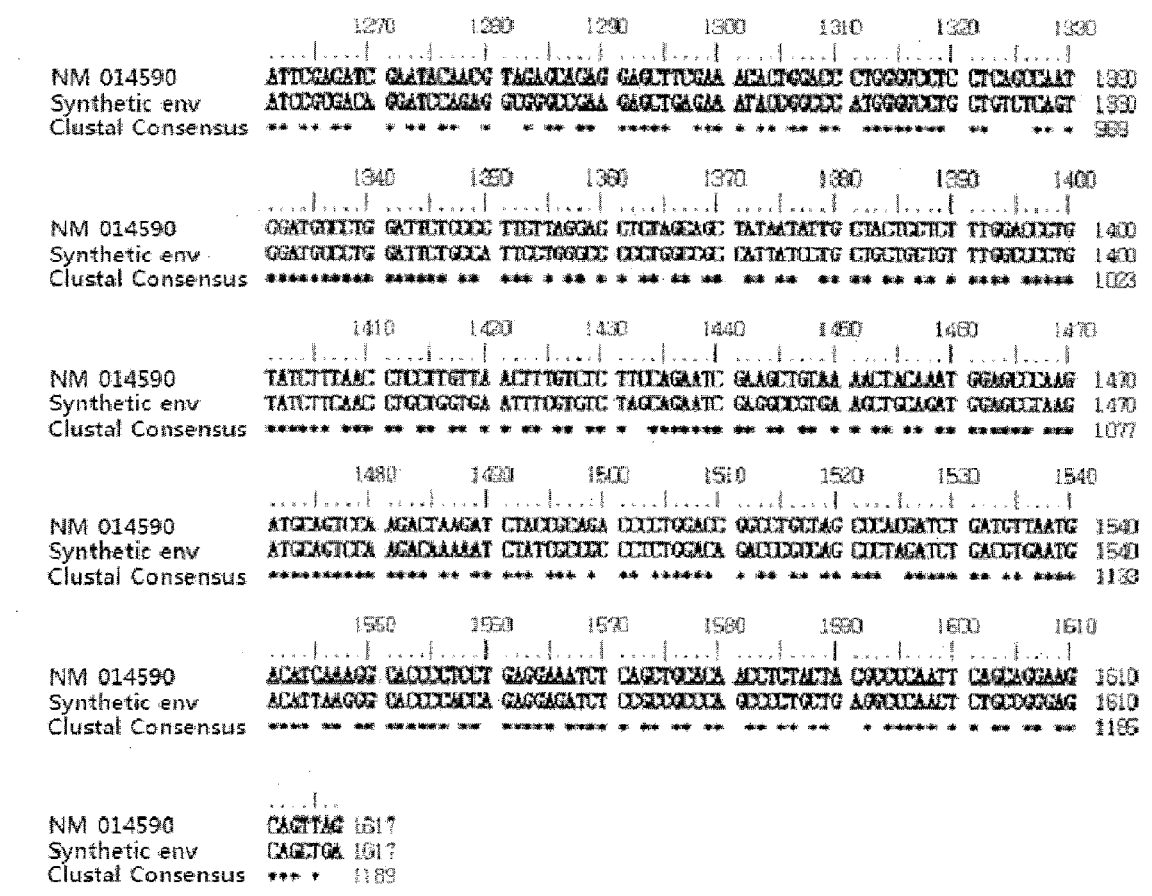

FIGS. 4-7 are a sequence homology through alignment of nucleotide sequence between a HERV envelope protein synthesized in the present invention (SEQ ID NO:1) and a HERV envelope protein. The nucleotide sequence of HERV envelope protein is shown in GenBank accession No. NM 014590 (SEQ ID NO:3).

Figure 1:
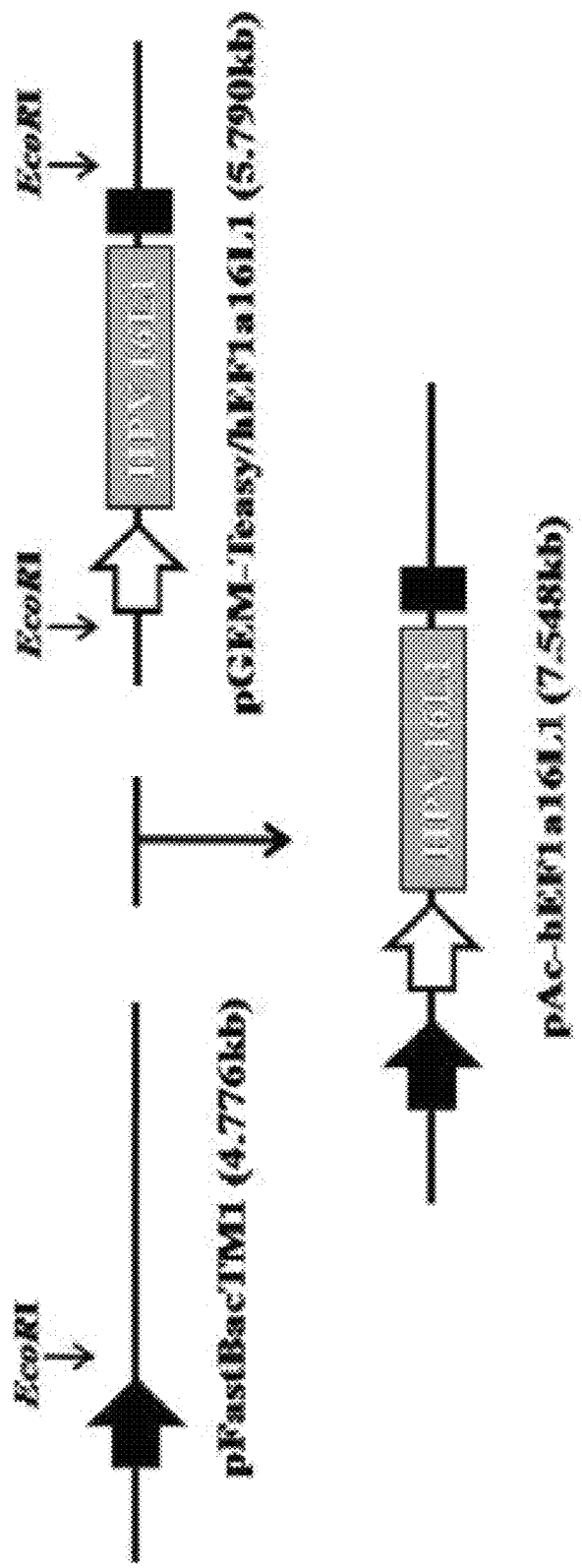
FIG. 1 schematically represents a construction procedure of transfer vector, pAc-hEF1α16L1, used in the present invention.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Cell Preparation

Insect cells, Sf9 (ATCC CRL-1711), were cultured in TC-100 media supplemented with 10% FBS (fetal bovine serum, Gibco BRL) and 1% penicillin/streptomycin (Gibco BRL) at 27° C. 293TT cells (Schiller Lab, USA NCI) were incubated in DMEM (Dulbecco's modified minimal essential medium) supplemented with 10% FBS and hygromycin B (400 µg/ml; Invitrogen Corp.). Human liver cell line, Huh7 cells (JCRB0403) were incubated in DMEM supplemented with 10% FBS (Gibco BRL) and 1% penicillin/streptomycin (Gibco BRL) at 37° C. under the atmosphere of 5% $CO_2$. HeLa cells (ATCC) were cultured in DMEM supplemented with 10% FBS, 100 U penicillin/ml, and 100 µg streptomycin/ml.

Synthesis of a Gene Encoding a HERV Envelope Protein

HERV (human endogenous retrovirus) is an endogenous virus in a human body, most of which are incorporated in human genome at an inactivated state. To obtain a HERV envelope protein, a gene encoding the HERV envelope protein was directly synthesized to optimize its nucleotide sequence suitable for expression in insect cells (GeneScript). The nucleotide sequence encoding the synthesized HERV envelope protein was inserted into EcoRV site of pUC57 vector (GeneScript), constructing pUC57-HERVenv.

Cloning of Transfer Vector

Construction of a recombinant baculovirus containing a procedure of transfer vector cloning were carried out according to Invitrogen's protocol using a Bac-to-Bac™ baculovirus expression system. To express HPV 16L1 protein in animal cells using the recombinant baculovirus system, a human elongation factor 1α (hEF1α) promoter and a HPV 16L1 gene were inserted into an AcMNPV (*autographa californica* multiple nuclear polyhedrosis virus) transfer vector. In PCR amplification, a plasmid DNA (p16L1L2) containing a 'hEF1α-HPV 16L1-hEF1α poly(A) signal' construct was used as a template (Schiller Lab, USA NCI; Christopher B. Buck et al., *J. Virol.* 82 (11): 5190-5197 (2008)). The primer sequence used was as follows: sense primer, 5'-GGCTCCGGTGCCCGTCAGTGGGCA-3' (SEQ ID NO:4); and antisense primer, 5'-TTAATTAAC-CCACGTTTCAACATG-3' (SEQ ID NO:5).

The PCR-amplified products were cloned into pGET-Teasy vector (Promega). The vector was restricted with EcoRI, and subsequently the fragments were inserted into EcoRI site of pFastBac™ 1 (Invitrogen) transfer vector, generating a pAc-hEF1α16L1 vector (See, FIG. 1). A HERV envelope protein gene was cut with SaiI from pUC57-HERVenv vector and then inserted into pFastBac™ 1 vector. After cutting pGEM-Teasy/hEF1α16L1 with NotI, hEF1α16L1 was inserted into pFastBac™ 1-HERVenv transfer vector, constructing pAcHERVenv-hEF1α16L1 vector (See, FIG. 2). To confirm OFR (open reading frame) of the transfer vectors cloned, gene sequences were analyzed using ABI gene sequence analyzer (ABI).

Construction of a Recombinant Baculovirus

Each recombinant transfer vectors cloned were transfected into DH10Bac (Invitrogen), producing recombinant bacmids (baculovirus shuttle vector). Selection of recombinant bacmids was carried out by PCR using M13 primer (Invitrogen). Three types of bacmids were transfected into Sf9 cells using lipofectamine (Invitrogen) for construction of recombinant baculoviruses. At 4 days post-infection, produced viruses were collected and infected repeatedly into new Sf9 cells to produce viruses with high titer. Afterwards, selected recombinant viruses were designated as AcHER-Venv-hEF1α16L1 and Ac-hEF1α16L1, respectively (See, FIG. 3). Finally, titers of recombinant baculoviruses were determined in Sf9 cells using a plaque assay. Meanwhile, recombinant baculoviruses (AcHERVenv-hEF1α18L1) were prepared according to the mentioned-above method for preparing recombinant baculoviruses (AcHERVenv-hEF1α16L1) except for using a HPV 18L1 gene (GenBank accession No. AY383629).

Transfection of a Gene into Huh7 Cells Using a Recombinant Baculovirus

Huh7 cells were seeded into a 24-well plate at a concentration of $1 \times 10^5$ cells/well and cultured at 37° C. After incubation for 12 hrs, the cells were washed with PBS, and then infected with Ac-hEF1α16L1 and AcHERVenv-hEF1α16L1 virus of 100 MOI (multiplicity of infectivity), respectively. Then, the cells were cultured at 37° C. for 10 hrs, and transferred to fresh DMEM supplemented with 10% FBS and 1% penicillin/streptomycin, followed by further incubation for 48 hrs. The extent of expression of HPV 16L1 was examined in each virus as follows.

Reverse Transcription-Polymerase Chain Reaction (RT-PCR) Analysis

Using RNeasy mini kit (Qiagen, Valencia, Calif.), total RNA was isolated from Huh7 cells transfected and DNA was removed by treatment of deoxyribonuclease I (DNaseI, Promega, Madison, Wis.). Purified RNA was reverse transcribed with M-MuLV reverse transcriptase (Bioneer, USA) to synthesize cDNA. 7.5 µl of PCR reaction mixture was mixed with 2.5 µl of cDNA and PCR was carried out using Thermal Cycler PCR (GeneAmp PCR system 9700, Perkin-Elmer Cetus, USA). PCR condition was as follows: hot-start step at 94° C. for 3 min; and 30-cycle step of denaturing at 94° C. for 30 sec, annealing at 62° C. for 20 sec and elongating at 72° C. for 20 sec. The primers used were: sense primer, 5'-CAGGGCCACAACAACGGCATCTGCTGGG-3' (SEQ ID NO:6); and antisense primer, 5'-GGCTGCAG-GCCGAAGTTCCAGTCCTCCA-3' (SEQ ID NO:7). The resulting PCR products were expected as about 275 bp. To normalize PCR efficiency between samples, 18S rRNA (ribosomal RNA) housekeeping gene was used. The amplified PCR products were detected on a 1.5% agarose gel.

Quantitative Analysis Using Real-Time PCR (Q-PCR)

To evaluate expression level of HPV 16L1 mRNA in cells infected, quantitative analysis using real-time PCR (Q-PCR) was performed as described previously (Dhar et al., 2001). The expression level of total HPV 16L1 mRNA was analyzed four-times using real-time PCR machine (Roter Gene 3000, Corbett Research, Australia). PCR reaction mixture was added with 5 µl of DyNAmo™ HS SYBR™ Green qPCR kit reaction solution and 5 µl of sample buffer containing primers and templates. The primers used were: 16L1 sense primer, 5'-CAGCGAGACCACCTACAAGA-3' (SEQ ID NO:8); and antisense primer, 5'-GCTGTTCAT-GCTGTGGATGT-3' (SEQ ID NO:9). The resulting PCR products were expected as about 138 bp. PCR products were obtained by pre-denaturing step at 95° C. for 5 min, and 45-cycle step of denaturing at 94° C. for 10 sec, annealing at 62° C. for 20 sec and elongating at 72° C. for 20 sec. After PCR reaction, the copy number and melting curve analysis of target molecules were performed using Roter-Gene ver. 6.0 program (Roter Gene 3000, Corbett Research, Australia).

Immunocytochemistry

Huh7 cells were divided into a glass slide, and then transfected with Ac-hEF1α16L1 and AcHERVenvhEF1α16L1 virus of 100 MOI (multiplicity of infectivity), respectively. After transfection for 48 hrs, the cells were fixed with 4% formaldehyde at 4° C. for 12 hrs, and washed with PBS (phosphate buffered saline), followed by further incubating with PBS containing 0.5% Triton X-100 at 37° C. for 10 min. Next, the cells were washed with PBS and blocked with PBS containing goat serum at 37° C. for 30 min, followed by incubating with HPV 16L1 monoclonal antibody (Camvir-1) at 4° C. overnight. The cells were washed with PBS for 30 min, and then incubated with a mouse IgG-horseradish peroxidase antibody for 1 hr. After washing with PBS, the cells were observed under a confocal laser scanning microscope (FV-1000 spectral, Olympus, Japan) to detect HPV 16L1 protein.

Gardasil

Gardasil™ (MERCK & CO, USA, MSD, Korea) as a HPV quadrivalent vaccine (type 6, 11, 16 and 18) served as a positive control of immune responses in this experiment.

Mouse

Four-week old female BALB/c mice were purchased from Orient-Bio Inc. (Korea), and housed under filter-tip conditions accessible in water and feed.

Mouse Immunization

Recombinant baculoviruses were diluted with sterile PBS at a total volume of 100 μl, and mice were immunized by intramuscular injection at the base of the bottom leg with viruses at a concentration of $10^7$ PFU (plaque forming unit). Twenty-four BALB/c mice were classified into eight groups (Table 1). Each mouse group was injected according to selected prime/boost regime. Immunization was carried out three-times at an interval of 2-week, and blood and vaginal washes were harvested at 1-week after each immunization. Before analysis, anti-serum was heat-denatured.

Table 1.

was added to each well. OPD (o-phenylenediamine) substrate in 0.1 M citrate buffer (pH 4.7) was added to each well, and then the absorbance was measured at 450 nm.

Pseudoviruses (PVs) Preparation

According the method proposed by Schiller (*J. Virol.* 78 (2): 751-757 (2004)), cotransfection of 293T cells was carried out to prepare PVs. 293T cells were seeded in 25 T flask 16 hrs before transfection, and transfected with the mixture of L1/L2-plasmid and pfwB plasmid expressing enhanced green fluorescent protein (GFP) using Lipofectin (Invitrogen). The nucleotide map of plasmids used is described in http://ccr.cancer.gov/Staff/links.asp?profileid=5637. To prepare HPV16 PVs, cells were transfected with 9 μg of each pfwB and p16L1/L2. In addition, cells were transfected with 9 μg of each pfwB and p18L1/L2 to prepare HPV18 PVs. After 4-6 hrs, the media of transfected cells were exchanged. The cells were harvested 48 hrs post-transfection. The supernatant was aliquoted and stored at −80° C. until next experiment.

Neutralization Analysis

The mixture of diluted serum of immunized mouse and PVs were incubated at room temperature for 1 hr., the mixture was inoculated into HeLa cells seeded at a concentration of $1 \times 10^4$ for 16 hrs before inoculation. After incubation for 2 days, GFP expression was observed under a fluorescence microscope. Neutralizing titer was indicated as a reciprocal of maximal dilution rate of serum which reduces GFP expression level to ½ level of sample treated with normal mouse serum.

IFN-γ Enzyme-Linked Immunospot (ELISPOT)

A 96-well plate was coated with 200 ng of anti-mouse IFN-γ capturing antibody (BD Bioscience) in 100 μl PBS at 4° C. overnight. The plate was blocked in 100 μl RPM' 1640 with 10% FBS at 37° C. for 2 hrs, and spleen cells with a

| Experimental group | Immunization (interval of 2-week) | | |
|---|---|---|---|
| | First | Second | Third |
| Group 1 | Gardasil | Gardasil | Gardasil |
| Group 2 | AcHERVenv-hEF1α16L1 or AcHERVenv-hEF1α18L1 | AcHERVenv-hEF1α16L1 or AcHERVenv-hEF1α18L1 | AcHERVenv-hEF1α16L1 or AcHERVenv-hEF1α18L1 |
| Group 3 | AcHERVenv-hEF1α16L1 or AcHERVenv-hEF1α18L1 | AcHERVenv-hEF1α16L1 or AcHERVenv-hEF1α18L1 | Gardasil |
| Group 4 | AcHERVenv-hEF1α16L1 or AcHERVenv-hEF1α18L1 | Gardasil | Gardasil |
| Group 5 | AcHERV | Gardasil | Gardasil |
| Group 6 | AcHERV | AcHERV | Gardasil |
| Group 7 | AcHERV | AcHERV | AcHERV |
| Group 8 | PBS | PBS | PBS |

ELISA

Sixty μl of MBP-L1 (Bioprogen Co., Ltd., Korea) that HPV16 L1 is linked to maltose binding protein (MBP) was added to each well of a ELISA plate at a concentration of 1 μg/ml, and incubated at 4° C. for 14-16 hrs. Each well was blocked at 37° C. for 2 hrs with a blocking buffer (5% skim milk in PBS containing 0.1% Tween-20). After washing with PBS containing 0.05% Tween-20 and 0.05% NP-40, serum samples diluted in blocking buffer (1:100) were added to each well, and incubated at room temperature for 1 hr. For IgG detection, anti-mouse IgG-HRP (SC-2030, Santa Cruz Biotechnology, Inc., Santa Cruz, Calif.) diluted in blocking buffer (1:2,000) was added to each well. To detect IgA, anti-mouse IgA-HRP (SC-3791, Santa Cruz Biotechnology, Inc., Santa Cruz, Calif.) diluted in blocking buffer (1:1,000)

density of $1 \times 10^6$ were seeded into the plate duplicate. PVs of $2 \times 10^6$ IFU (infectious unit) were inoculated into the plate, followed by incubating at 37° C. for 24 hrs. The plate was washed with PBS containing 0.05% Tween 20 three times to remove the cells. Each well was added with 20 ng of sterile-filtered anti-mouse IFN-γ detecting antibody in PBS with 10% FBS, and then incubated at room temperature for 2 hrs. After the plate was washed with PBS containing 0.05% Tween 20 three times, 100 μl dilution solution of streptavidin-alkaline phosphatase (1:1,000) was added. The plate was incubated at room temperature for 1 hr, and washed with PBS containing 0.05% Tween 20 three times, followed by washing with PBS three times. The plate was added with 100 μl of AEC substrate reagent (BD Biosciences, CA, USA) and incubated for 10 min. The plate was washed with distilled water to stop reaction. The spot was quantitated using an ELISPOT reader (AID Elispot Reader ver. 4, Germany). The well containing media without treatment of spleen cells served as a negative control. The count of background well was depreciated from samples.

Results

Gene Synthesis of a HERV Envelope Protein

For construction of a transfer vector, a HERV envelope protein gene (Env) was prepared through gene synthesis, and optimized for codon usage of insect to be effectively expressed in insect cells. Likewise, the amino acid sequence of synthetic HERV envelope protein was partially modified in a state maintaining the amino acid sequence of HERV envelope protein as described previously. The nucleotide sequence and amino acid sequence of HERV envelope protein (1,617 bp in length) used in the present invention are described in SEQ ID NO:1 and SEQ ID NO:2, respectively. As shown in FIGS. 4-7, the nucleotide sequence of synthetic HERV envelope protein was compared with that of conventional HER envelope protein, suggesting a homology of 73.5% in the level of nucleotide sequence.

Construction of a Recombinant Baculovirus

Figure 2:
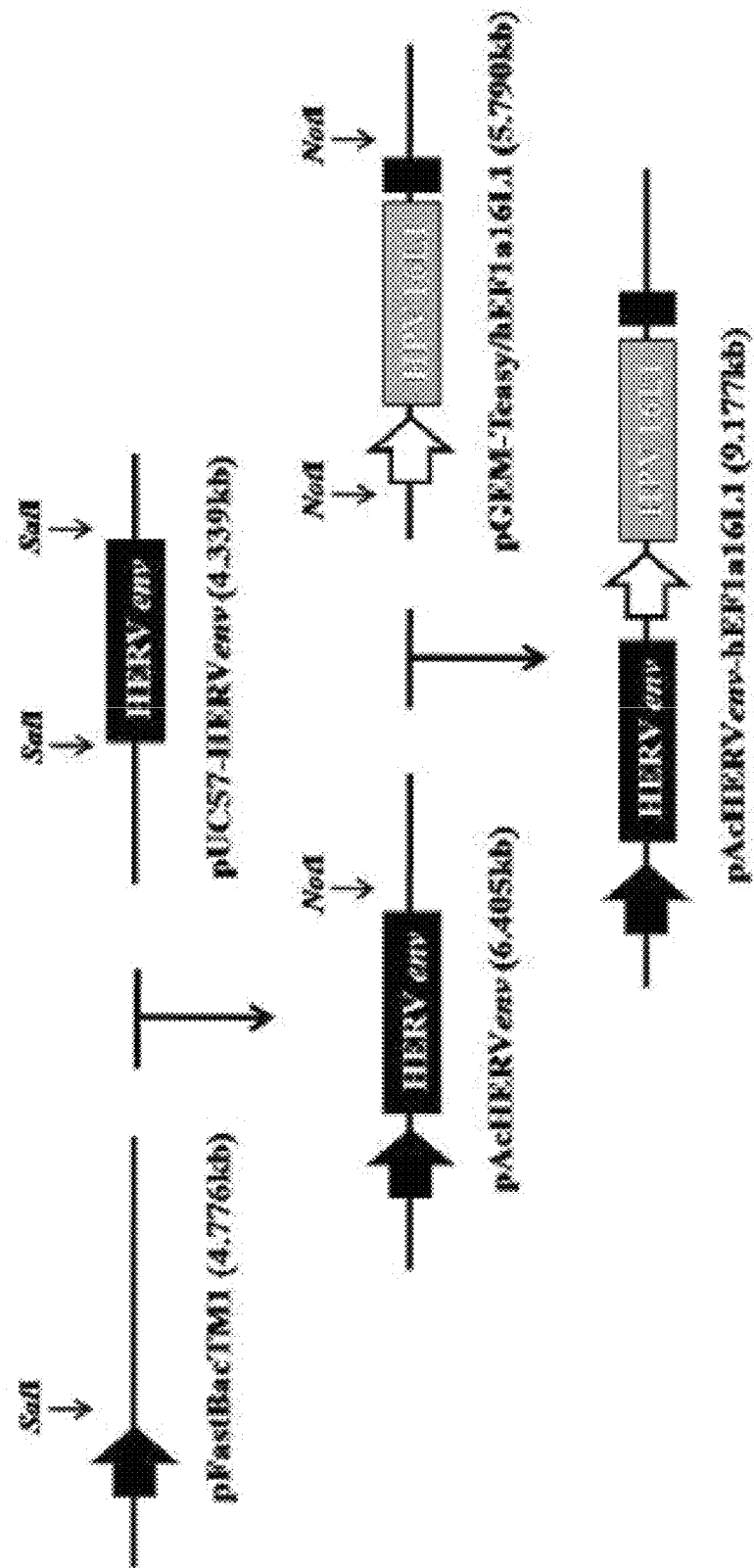
FIG. 2 schematically represents a construction procedure of transfer vector, pAcHERVenv-hEF1α16L1, used in the present invention.
Figure 3:
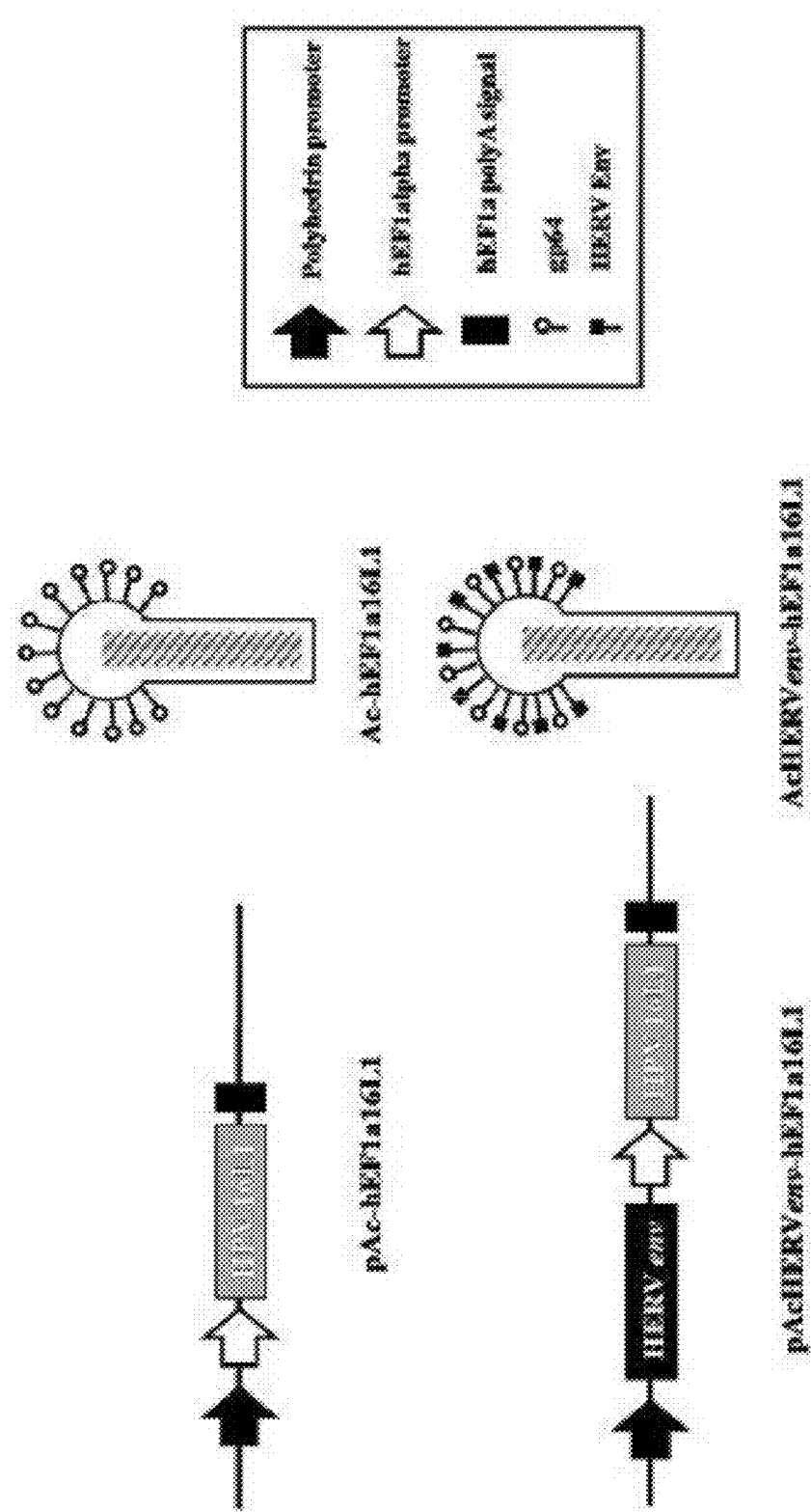
FIG. 3 represents an expected scheme of chimera baculovirus transfer vectors and viruses including pAc-hEF1α16L1 and pAcHERVenv-hEF1α16L1 construct, respectively.

To construct recombinant baculoviruses, two types of transfer vectors, pAc-hEF1α16L1 and pAcHERVenv, hEF1α16L1, were planned, and expected forms of baculoviruses were indicated (FIG. 3). To insert an envelope protein of baculovirus, a polyhedrin promoter was followed by inserting a gene of HERV envelope protein (Env), and a HPV 16L1 gene was controlled by hEF1α. HERV Env may induce a receptor-mediated phagocytosis in human cells. FIG. 1 schematically represents a cloning method of pAc-hEF1α16L1, and FIG. 2 briefly represents a cloning method of pAcHERVenv-hEF1α16L1. The cloning of pAcHER-Venv-hEF1α18L1 was performed according to the same method.

Under regulation of an insect virus promoter, HERV envelope protein has characteristics of being highly expressed in insect cells but being hardly expressed in animal cells. On the contrary, HPV 16L1 protein is possible to be highly efficiently expressed in animal cells but being hardly or very lowly expressed in insect cells due to utilization of human elongation factor 10 promoter (hEF1α). Recombinant bacmids were prepared using each plasmid cloned, and transfected into Sf9 cells, producing viruses with higher titer.

Efficiency Measurement for Transfection of HPV 16L1 Gene to Huh7 Cells

Figure 8:
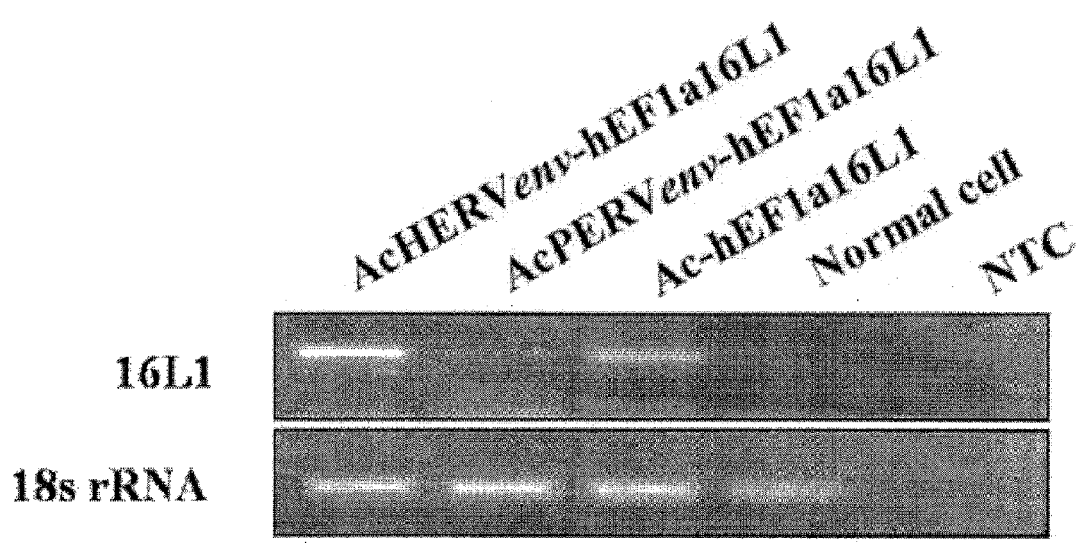
FIG. 8 represents RT-PCR to examine expression of HPV 16L1 gene in Huh7 cells infected with Ac-hEF1α16L1 or AcHERVenv-hEF1α16L1 construct. "NTC" indicates a control without template. AcHERVenv-hEF1α16L1 construct contains an envelope protein of pig endogenous retrovirus and exhibits almost no infectivity to human Huh7 cells.

To check transfection efficiency of HPV 16L1 gene according to modification of baculovirus envelope, Huh7 cells were infected with Ac-hEF1α16L1 and AcHERVenv-hEF1α16L1 virus at MOI of 100, respectively. Expression level of HPV 16L1 mRNA was examined using RT-PCR. As shown in FIG. 8, HPV 16L1 products of about 275 bp in length were detected in cells infected with Ac-hEF1α16L1 and AcHERVenv-hEF1α16L1 virus using electrophoresis. However, there was a difference to what extent HPV 16L1 gene was amplified. The amplified amount of HPV 16L1 gene in AcHERVenv-hEF1α16L1 baculovirus having HERV envelope protein in its envelope was higher than that in baculovirus having no modification in its envelope.

Figure 9:
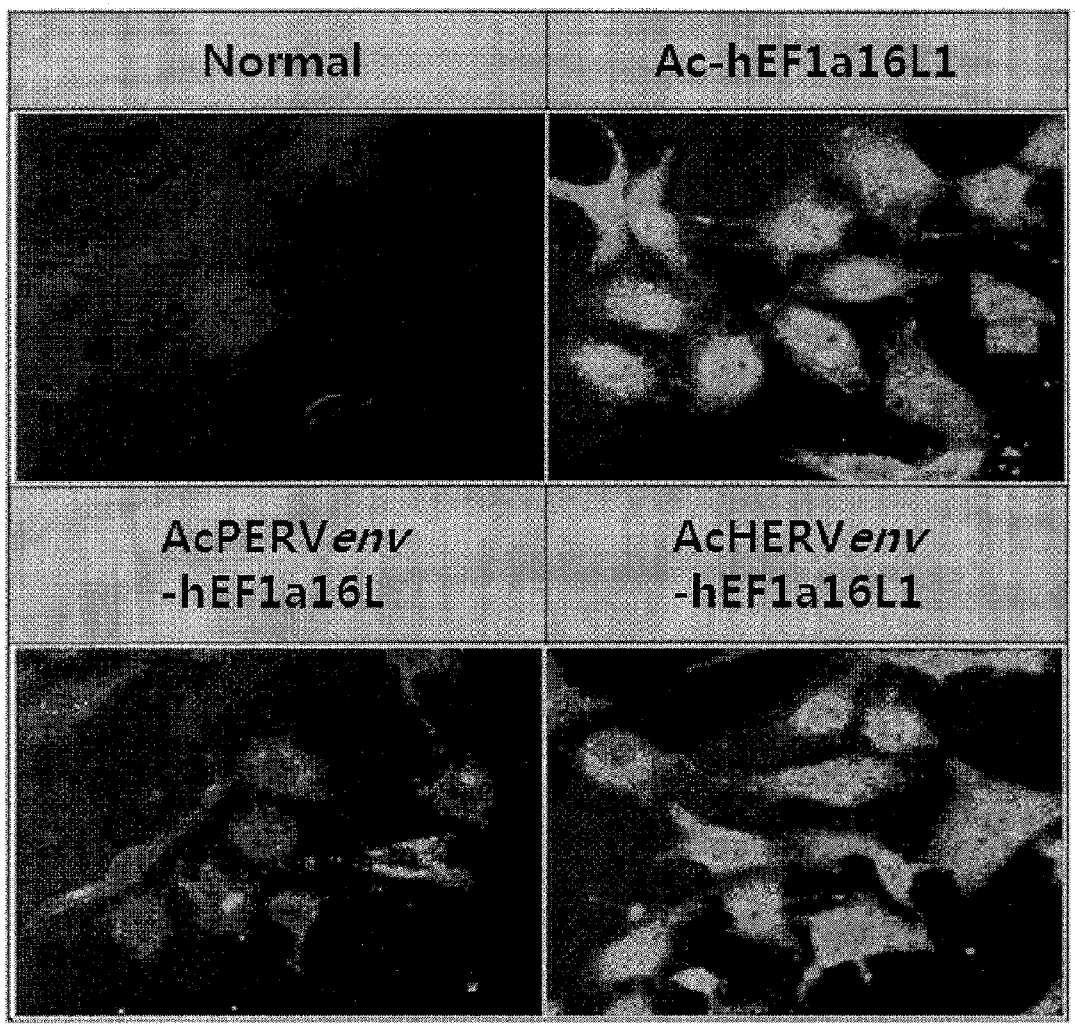
FIG. 9 is images analyzing HPV 16L1 of normal Huh7 cells and Huh7 cells infected with Ac-hEF1α16L1 or AcHERVenv-hEF1α16L1 construct through immunocytochemical staining. AcHERVenv-hEF1α16L1 construct contains an envelope protein of pig endogenous retrovirus and exhibits almost no infectivity to human Huh7 cells.

Immunocytochemistry analysis was carried out to observe under a microscope in Huh7 cells infected with Ac-hEF1α16L1 and AcHERVenv-hEF1α16L1 virus. At 48 hrs after infection, the cells were stained with a HPV 16L1 monoclonal antibody (Camvir-1) and a mouse IgG-horseradish peroxidase antibody, and observed under a confocal laser scanning microscope to determine whether HPV 16L1 protein is or not. As shown in FIG. 9, it could be demonstrated that the fluorescence was overall detected in the cells infected with HERVenv-hEF1α16L1 and Ac-hEF1α16L1 virus compared to Huh7 cells having no virus infection. However, the following experiments were further performed to significantly differentiate the extent of fluorescence between two samples.

Figure 10:
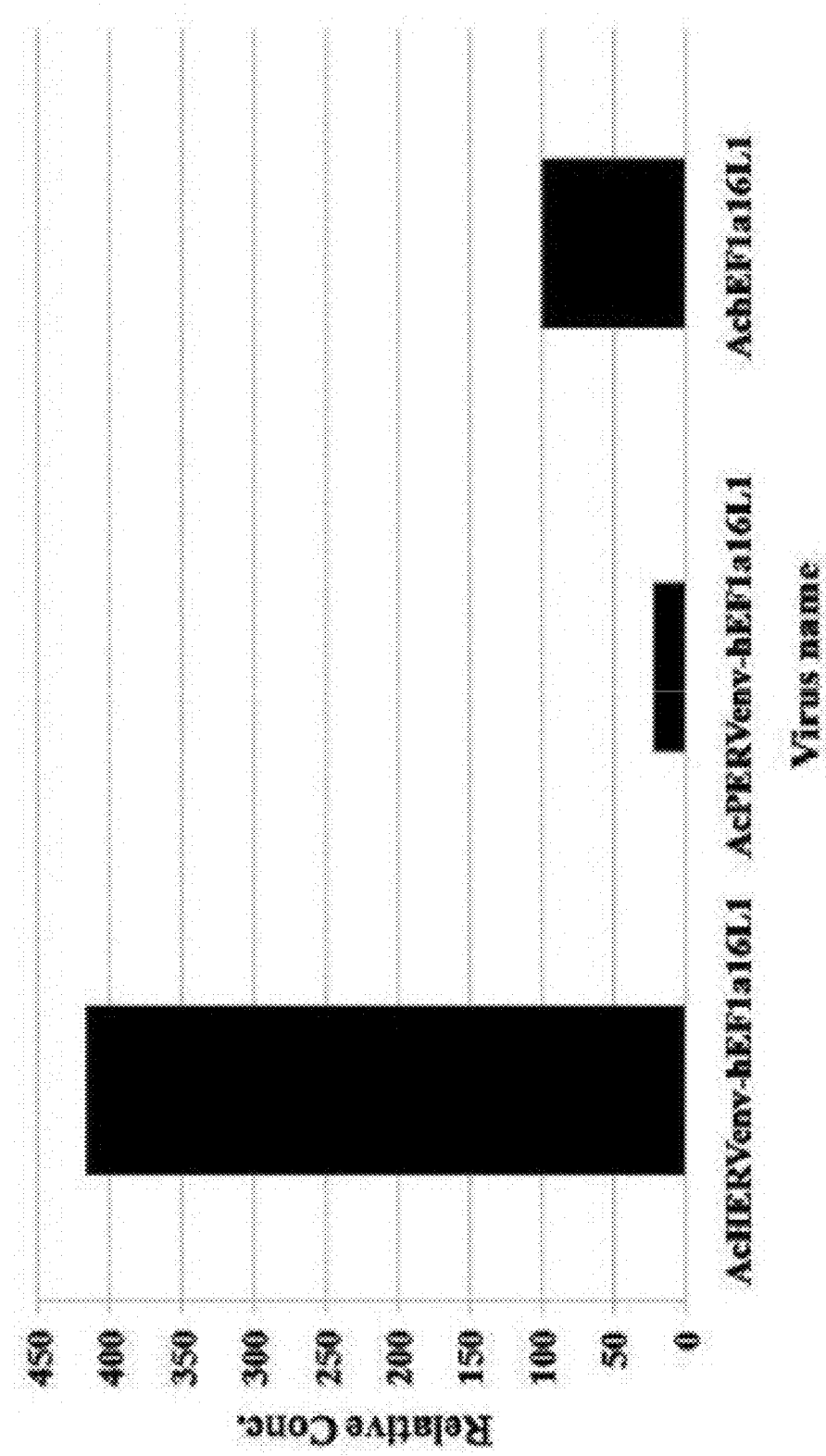
FIG. 10 is a bar graph showing quantitative analysis by real-time PCR using a Delta-Delta CT method to determine expression level of HPV 16L1 mRNA in Huh7 cells infected with Ac-hEF1α16L1 or AcHERVenv-hEF1α16L1 construct. AcHERVenv-hEF1α16L1 construct contains an envelope protein of pig endogenous retrovirus and exhibits almost no infectivity to human Huh7 cells.
Figure 11:
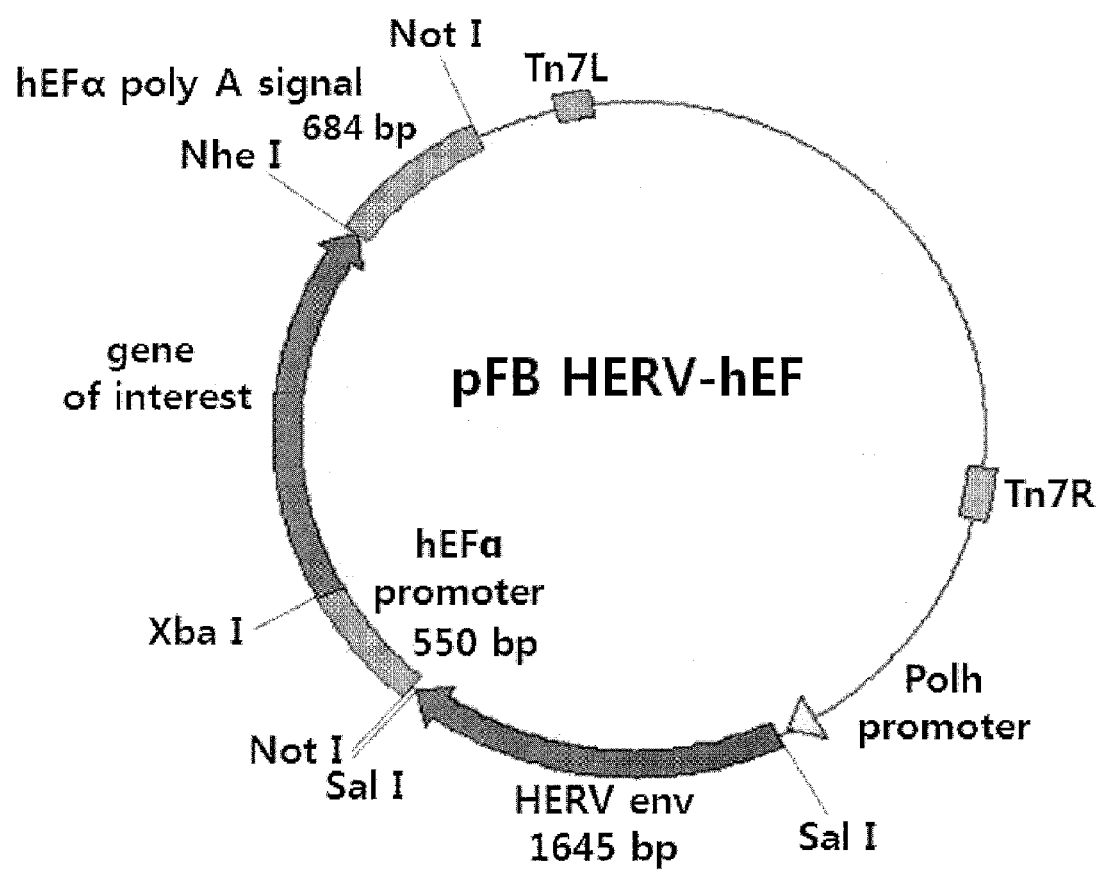
FIG. 11 represents a gene map of vector pFB HERV-hEF constructed in an embodiment of the present invention. Abbreviation: Polh promoter, polyhedrin promoter; HERVenv, envelope gene of HERV; Tn7R, right arm; and Tn7L, left arm. In AcHERVenv-hEF1α16L1 construct, HPV 16L1 is positioned at a gene of interest.

To determine a transfer efficiency of HPV 16L1 gene using infection, quantitative analysis by real-time PCR (Q-PCR) was carried out. The accuracy of Q-PCR analysis was normalized by a standard curve. The experiments were repeated four times, and relative quantitation was obtained from a Delta-Delta CT method using Roter-*Gene* ver. 6.0 as shown in FIG. 10. As described in the following table 2, it could be appreciated that where the gene copy number in cells infected with Ac-hEF1α16L1 virus is considered as 1, the gene copy number in cells infected with AcHERVenv-hEF1α16L1 virus is evaluated as 4.17-fold.

TABLE 2

| Virus name | GOI CT | GOI count | Norm. CT | ΔCT | Δ-ΔCT | Relative concentration | Normalization |
|---|---|---|---|---|---|---|---|
| AcHERVenv-hEF1α16L1 | 22.89 | 2 | 19.45 | 3.44 | −2.06 | 4.17 | — |
| AcPERVenv-hEF1α16L1 | 25.85 | 2 | 18.24 | 7.61 | 2.11 | 0.23 | — |
| AchEF1α16L1 | 23.93 | 2 | 18.44 | 5.5 | 0 | 1 | Yes |

Immune Response in Mouse

Figure 12:
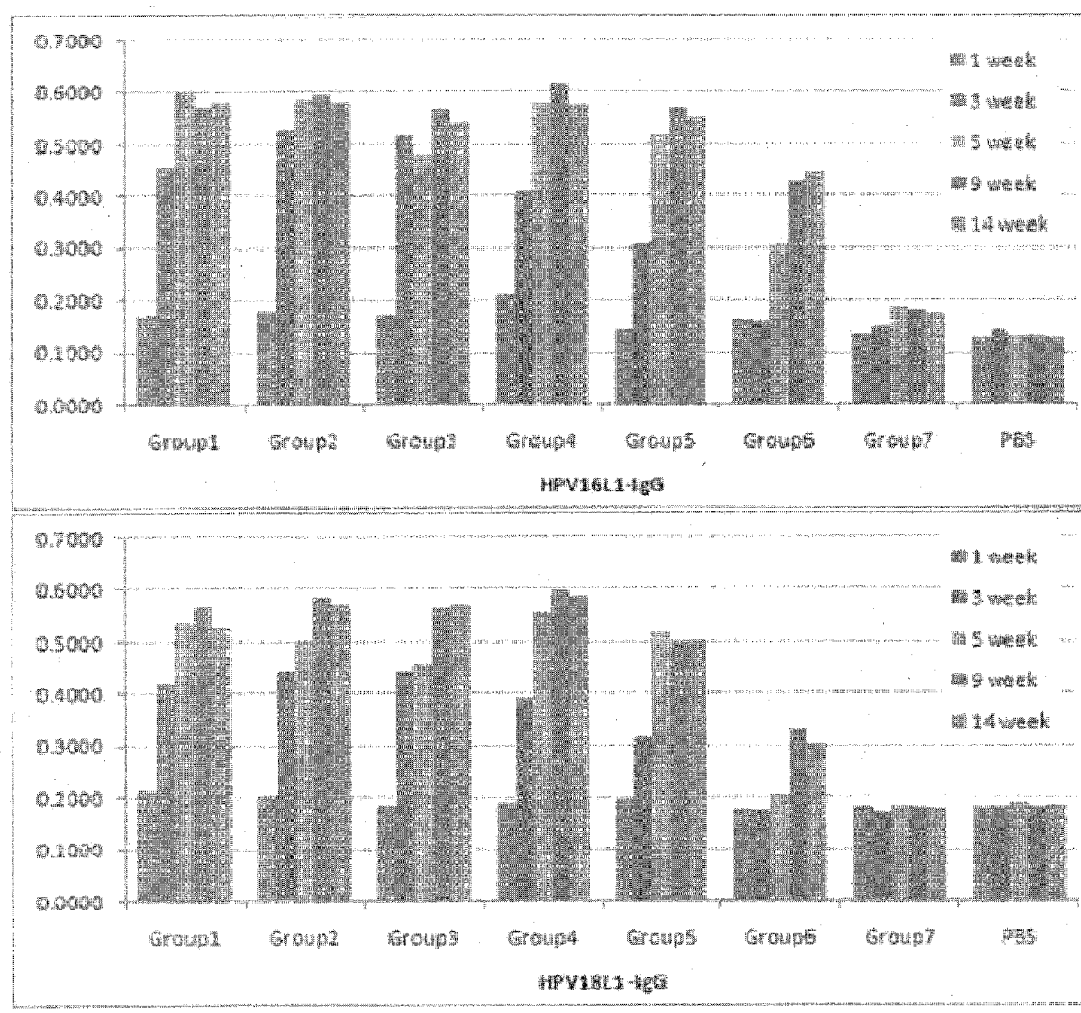
FIG. 12 represents ELISA for IgG antibody response in serum immunized with chimera baculovirus of the present invention. Sample and anti-mouse IgG were used at a dilution ratio of 1:100 and 1:2,000, respectively. The bars from left to right correspond to 1-week, 3-week, 5-week, 9-week and 14-week in each group.

Mouse was intramuscularly injected with AcHERVenv, AcHERVenv-hEF1α16L1, or AcHERVenv-hEF1α18L1 at a concentration of $10^7$ PFU. Gardasil-injected group was used as a positive control, and AcHERVenv- or PBS-injected group served as a negative control. Immune responses of each group were compared. HPV16L1-specific IgG antibody or HPV18L1-specific IgG antibody were detected from mouse serum immunized using ELISA. Prior to immunization, noticeably low level of IgG antibody was detected in the serum from AcHERVenv- or PBS-injected group as expected. As shown in FIG. 12, IgG antibody response was detected in only serum of gardasil-injected group (Group 1) after first immunization, whereas not significantly in serum of the group injected with AcHERVenv-hEF1α16L1 or AcHERVenv-hEF1α18L1 (Group 2). IgG antibody response against HPV16 and HPV18 in serum of mouse immunized with gardasil two-times, was enhanced about 2.7-fold and 2-fold higher than that in serum of mouse after first immunization, respectively. In serum of mouse immunized with gardasil three-times, IgG antibody response against HPV16 and HPV18 was enhanced about 1.3-fold and 1.3-fold higher than that in serum of mouse after second immunization, and 3.5-fold and 2.5-fold higher than that in serum of mouse after second immunization, respectively (See, Group 1 in FIG. 12). IgG antibody response against HPV16 and HPV18 in serum of mouse immunized with AcHERVenv-hEF1α16L1 or AcHERVenv-hEF1α18L1 two-times, was enhanced about 3-fold and 2-fold higher than that in serum of mouse after first immunization, respectively. In serum of mouse immunized with AcHERVenv-hEF1α16L1 or AcHERVenv-hEF1α18L1 three-times, IgG antibody response against HPV16 and HPV18 was enhanced about 1.1-fold and 1.1-fold higher than that in serum of mouse after second immunization, and 3.3-fold and 2.4-fold higher than that in serum of mouse after second immunization, respectively (See, Group 2 in FIG. 12). Therefore, it could be appreciated that IgG antibody response against HPV16 and HPV18 in serum of mouse immunized with AcHERVenv-hEF1α16L1 or AcHERVenv-hEF1α18L1 is similar to that immunized with gardasil. Given that IgG antibody response was also observed in 9-week and 14-week after first immunization, it was evident that the immunity was continuously maintained.

Figure 13:
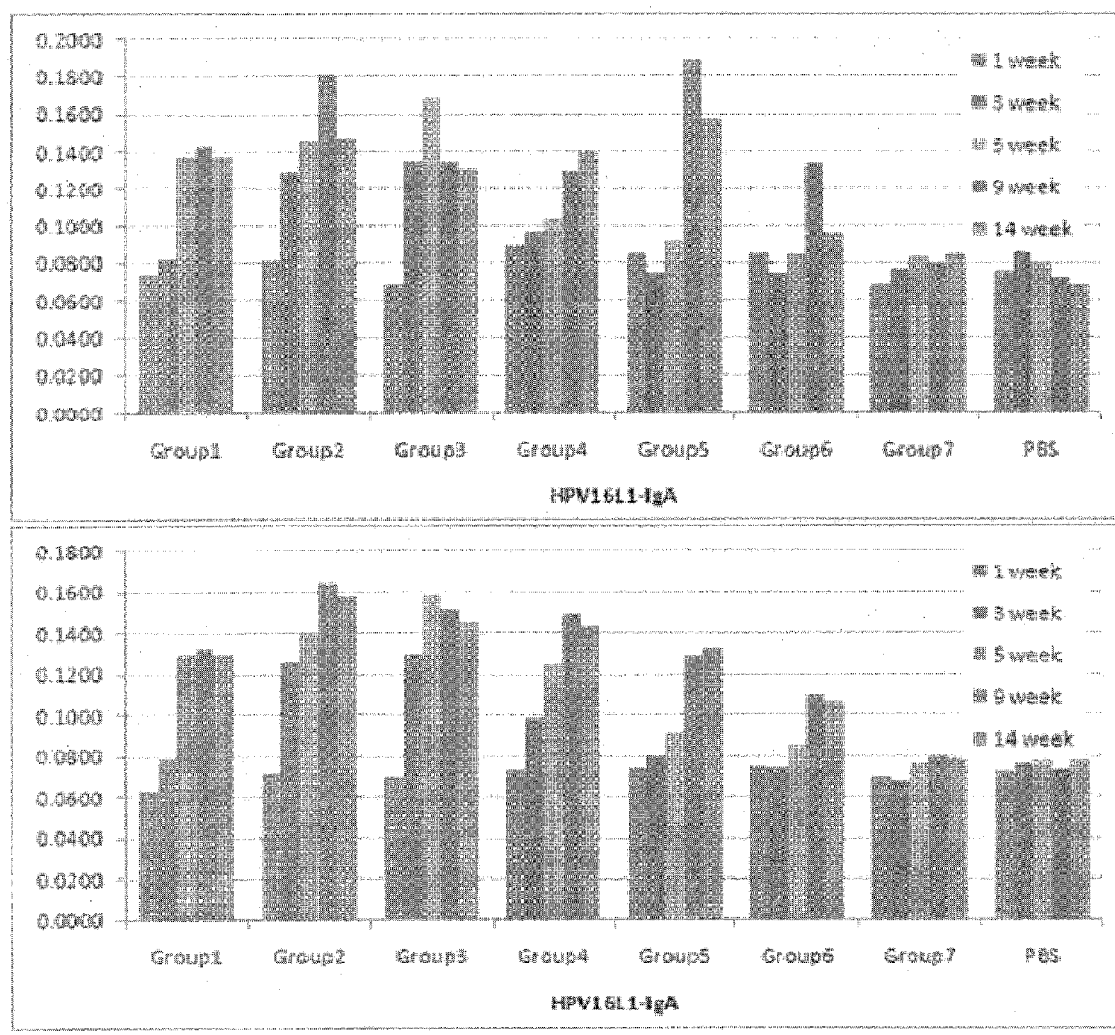
FIG. 13 is to measure IgG antibody response in vaginal washing solution immunized with chimera baculovirus of the present invention. Sample and anti-mouse IgG were used at a dilution ratio of 1:50 and 1:1,000, respectively. The y axis indicates absorbance at 405 nm. The bars from left to right correspond to 1-week, 3-week, 5-week, 9-week and 14-week in each group.

Secretory IgA response was determined by ELISA using vaginal washes of immunized mouse. It was demonstrated that IgA antibody is secreted not only in the gardasil-injected experimental group but also in the experimental group injected with AcHERVenv-hEF1α16L1 or AcHERVenv-hEF1α18L1 (FIG. 13). It was evident that in addition to first immunization, IgA antibody secretion was also increased in second and third immunization, and further the immunity was persisted because IgA antibody response was observed in 9-week and 14-week. Hence, it could be appreciated that the immunization with AcHERVenv-hEF1α16L1 or AcHERVenv-hEF1α18L1 may induce mucosal immune response in mouse.

Neutralization of HPV Type 16, HPV Type 18, and BPV PVs by Mouse Anti-Serum

Figure 14:
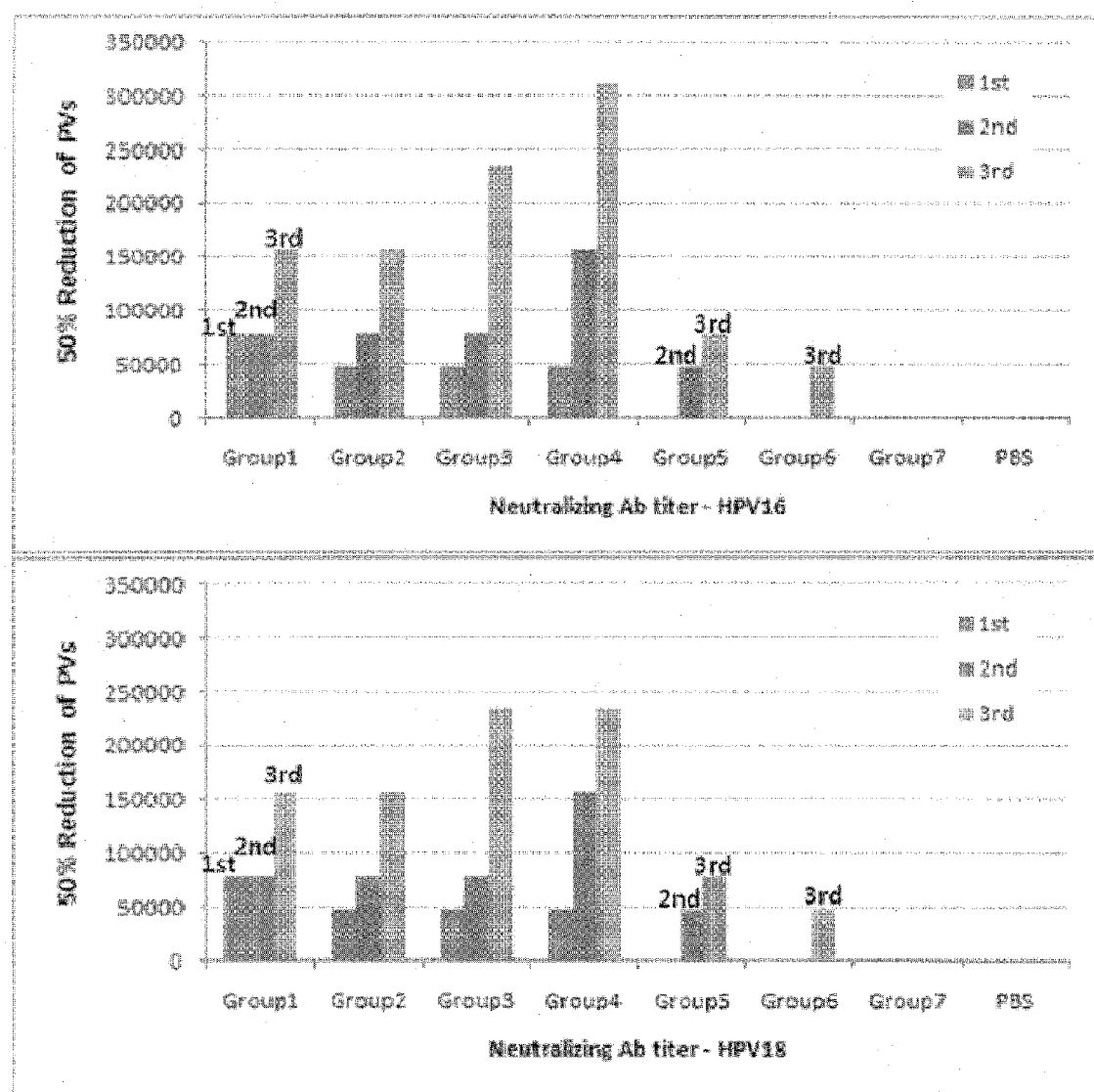
FIG. 14 represents neutralization response against HPV16 or HPV18 PVs (pseudoviruses) by mouse antiserum immunized with chimera baculovirus of the present invention.

Neutralizing activity of anti-serum was determined depending on the extent of inhibiting infectivity of HPV16 or HPV18 PVs against GFP-expressing plasmid in HeLa cells. Titer of neutralizing antibody was indicated as a reciprocal of serum amount under conditions that serum is maximally diluted (i.e., serum diluted at a multiple of 5) and GFP expression level of samples with serum treatment is reduced to 50% or 90% compared to that of samples without serum treatment. Neutralizing activity of diluted serum against HPV16 or HPV18 PVs in each experimental group is shown in FIG. 14. FIG. 14 represents a neutralization titer that HPV16 or HPV18 PVs were reduced to 50%, and neutralizing antibody titers after second and third immunization than first immunization were highly enhanced in all experimental groups. After third immunization, neutralizing antibody titer in Group 1 and 2 was 156,250, and observed in higher level without significant difference in B cell humoral immune responses between gardasil-injected group and group injected with AcHERVenv-hEF1α16L1 or AcHERVenv-hEF1α18L1 developed in the present invention. Considered standard as 50% of neutralizing activity, in Group 3 and 4 boosted with gardasil after priming of AcHERVenv-hEF1α16L1 or AcHERVenv-hEF1α18L1, neutralizing antibody titer was further increased from 234,375 to 312,500. Interestingly, in Group 4 boosted with gardasil two-times after priming of AcHERVenv-hEF1α16L1, neutralizing antibody titer was measured at the highest titer of 312,500. As results, it is expected that the priming of AcHERVenv-hEF1α16L1 may improve boosting effect of gardasil.

Cellular Immune Response Analysis

Figure 15:
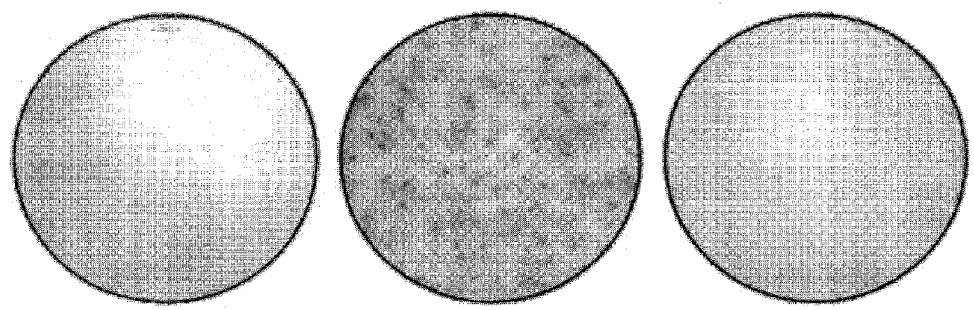
FIG. 15 represents ELISPOT analysis for cell-mediated immune response. To evaluate IFN-γ expression, ELISPOT was carried out in spleen cells. CD8$^+$ T cells were stimulated with HPV 16 PVs or HPV18 PVs. (A) indicates an experimental group immunized with gardasil, (B) indicates an experimental group immunized with AcHERVenv-hEF1α16L1 or AcHERVenv-hEF1α18L1, and (C) serves as a control.
Figure 15:
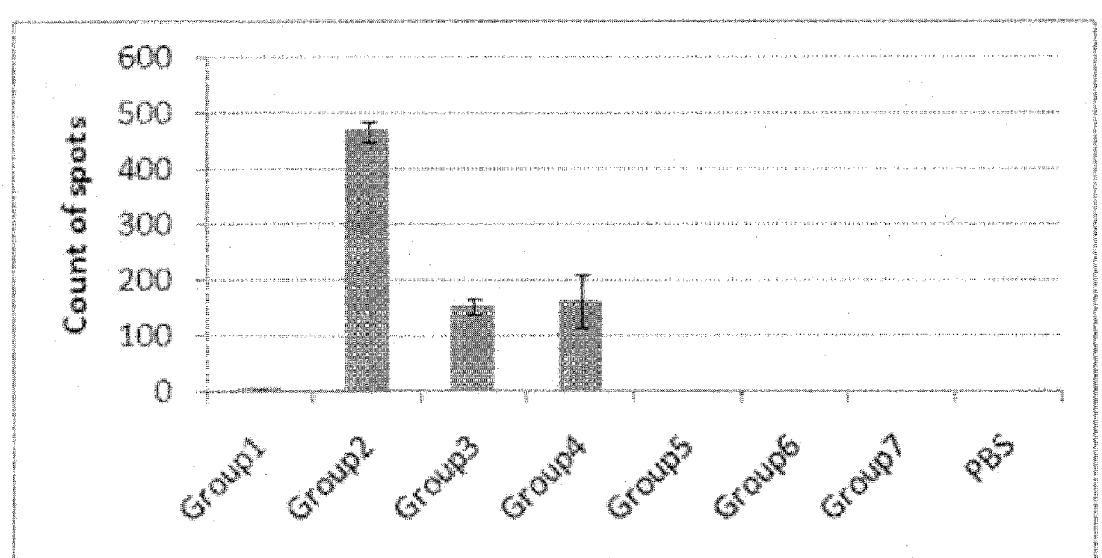

To assess T-cell immune responses in immunized mouse, ELISPOT analysis was carried out. About 500 spots were observed in spleen cells (1×10⁶) of mouse in Group 2 immunized with AcHERVenv-hEFα16L1 or AcHERVenv-hEF1α18L1 three-times, whereas no spot was observed in Group 1 immunized with gardasil or a negative control due to secretion of IFN-γ. Of mice injected with gardasil, AcHERVenv-hEFα16L1 or AcHERVenv-hEF1α18L1, and PBS, strong HPV16-specific T-cell response (secretion of IFN-γ) was generated in mice immunized with AcHERVenv-hEFα16L1 or AcHERVenv-hEF1α18L1, and no cellular immune responses were detected in the experimental group immunized with gardasil (FIG. 15).

In conclusion, AcHERVenv-hEFα16L1 or AcHERVenv-hEF1α18L1 chimera baculovirus effectively transferred a DNA vaccine into an animal body in a stable manner, leading to almost similar effect on humoral immune responses compared with conventional vaccine, gardasil. Inoculation of both AcHERVenv-hEFα16L1 or AcHERVenv-hEF1α18L1 chimera baculovirus and gardasil resulted in much higher neutralizing antibody titer than that of gardasil alone. As expected, gardasil generated no cellular immunity, whereas AcHERVenv-hEFα16L1 or AcHERVenv-hEF1α18L1 chimera baculovirus permits to express L1 gene in APC (antigen presentation cell) as a DNA vaccine, inducing very strong cellular immunity. Taken together, a novel AcHERVenv-hEFα16L1 or AcHERVenv-hEF1α18L1 chimera baculovirus vaccine of the present invention is more stable and economic than gardasil in respect of vaccine efficacy.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Abe T, Takahashi H, Hamazaki H, Miyano-Kurosaki N, Matsuura Y, Takaku H. (2003) Baculovirus induces an innate immune response and confers protection from lethal influenza virus infection in mice. *Journal of Immunology*, 171: 1133-1139.

Ault K A, Giuliano A R, Edwards R P, Tamms G, Kim L L, Smith J F, Jansen K U, Allende M, Taddeo F J, Skulsky D, Barr E. (2004) A phase I study to evaluate a human papillomavirus (HPV) type 18 L1 VLP vaccine. *Vaccine* 22(23-24):3004-7.

Baskin L S, Yucel S, Cunha G R, Glickman S E, Place N J. (2006) A neuroanatomical comparison of humans and spotted hyena, a natural animal model for common urogenital sinus: clinical reflections on feminizing genitoplasty. *J Urol.* 175(1):276-83.

Barsoum, J., Brown, R., McKee, M. and Boyce, F. M. (1997) Efficient transduction of mammalian cells by a recombinant baculovirus having the vesicular stomatitis virus G glycoprotein. *Hum Gene Ther* 8, 2011-2018.

Blissard, G. W. and Wenz, 3. R. (1992) Baculovirus gp64 envelope glycoprotein is sufficient to mediate pH-dependent membrane fusion. *J Virol* 66, 6829-6835.

Boyce, F. M. and Bucher, N. L. (1996) Baculovirus-mediated gene transfer into mammalian cells. *Proc Natl Acad Sci USA* 93, 2348-2352.

Condreay, J. P., Witherspoon, S. M., Clay, W. C. and Kost, T. A. (1999) Transient and stable gene expression in mammalian cells transduced with a recombinant baculovirus vector. *Proc Natl Acad Sci USA* 96, 127-132.

Daftarian P, Mansour M, Benoit A C, Pohajdak B, Hoskin D W, Brown R G, Kast W M. (2006) Eradication of established HPV 16-expressing tumors by a single administration of a vaccine composed of a liposome-encapsulated CTL-T helper fusion peptide in a water-in-oil emulsion. Vaccine. 24(24):5235-44.

Dhar, A. K., Roux, M. M. and Klimpel, K. R. (2001) Detection and quantification of infectious hypodermal and hematopoietic necrosis virus and white spot virus in shrimp using real-time quantitative PCR and SYBR Green chemistry. *J Clin Microbiol* 39, 2835-2845.

Facciabene A, Aurisicchio L, La Monica N. (2004) Baculovirus vectors elicit antigen-specific immune responses in mice. Journal of Virology, 78(16):8663-8672.

Gambhira R, Karanam B, Jagu S, Roberts J N, Buck C B, Bossis I, Alphs H, Culp T, Christensen N D, Roden R B. (2007) A protective and broadly cross-neutralizing epitope of human papillomavirus L2. Journal of virology, 81 (24); 13927-13931.

Hofmann, C., Sandig, V., Jennings, G., Rudolph, M., Schlag, P. and Strauss, M. (1995) Efficient gene transfer into human hepatocytes by baculovirus vectors. *Proc Natl Acad Sci USA* 92, 10099-10103.

Kondo K, Ochi H, Matsumoto T, Yoshikawa H, Kanda T. (2008) Modification of human papillomavirus-like particle vaccine by insertion of the cross-reactive L2-epitopes. *Journal of Medical Virology* 80, 841846.

Kost, T. A. and Condreay, J. P. (2002) Recombinant baculoviruses as mammalian cell gene-delivery vectors. *Trends Biotechnol* 20, 173-180.

Kumar M, Bradow B P, Zimmerberg J. (2003) Large-scale production of pseudotyped lentiviral vectors using baculovirus GP64. *Hum Gene Ther.* 14(1):67-77.

Lin, S. W., Hensley, S. E., Tatsis, N., Lasaro, M. O. and Ertl, H. C. (2007) Recombinant adeno-associated virus vectors induce functionally impaired transgene product-specific CD8 T cells in mice. *J Clin Invest* 117, 3958-3970.

Lung O, Westenberg M, Vlak J M, Zuidema D, Blissard G W. (2002) Pseudotyping *Autographa californica* multicapsid nucleopolyhedrovirus (AcMNPV): F proteins from group II NPVs are functionally analogous to AcMNPV GP64. *Journal of Virology,* 76(11):5729-5736.

Mangor J T, Monsma S A, Johnson M C, Blissard G W. (2001) A GP64-null baculovirus pseudotyped with vesicular stomatitis virus G protein. *Journal of Virology* 75(6):2544-2556.

Monahan, P. E., Jooss, K. and Sands, M. S. (2002) Safety of adeno-associated virus gene therapy vectors: a current evaluation. *Expert Opin Drug Saf* 1, 79-91.

Monsma, S. A., Oomens, A. G. and Blissard, G. W. (1996) The GP64 envelope fusion protein is an essential baculovirus protein required for cell-to-cell transmission of infection. *J Virol* 70, 4607-4616.

Mulligan R C. (1993) The basic science of gene therapy. *Science* 260(5110):926-932.

Park S W, Lee H K, Kim T G, Yoon S K, Paik S Y. (2001) Hepatocyte-specific gene expression by baculovirus pseudotyped with vesicular stomatitis virus envelope glycoprotein. *Biochemical and Biophysical Research Communications* 289(2):444-450.

Pastrana D V, Buck C B, Pang Y Y, Thompson C D, Castle P E, FitzGerald P C, KrKjaer S, Lowy D R, Schiller J T. (2004) Reactivity of human sera in a sensitive, high-throughput pseudovirus-based papillomavirus neutralization assay for HPV16 and HPV18. Virology 321, 205-216.

Ratish Gambhira, Balasubramanyam Karanam, Subhashini Jagu, Jeffrey N. Roberts, Christopher. Buck, Ioannis Bossis, Hannah Alphs, Timothy Culp, Neil D. Christensen, and Richard B. S. Roden (2007) A Protective and Broadly Cross-Neutralizing Epitope of Human Papillomavirus L2. *Journal of Virology* 81(24): 13927-13931.

Sandig, V., Hofmann, C., Steinert, S., Jennings, G., Schlag, P. and Strauss, M. (1996) Gene transfer into hepatocytes and human liver tissue by baculovirus vectors. *Hum Gene Ther* 7, 1937-1945.

Tjia, S. T., zu Altenschildesche, G. M. and Doerfler, W. (1983) *Autographa californica* nuclear polyhedrosis virus (AcNPV) DNA does not persist in mass cultures of mammalian cells. *Virology* 125, 107-117.

Vogt, S., Ueblacker, P., Geis, C., Wagner, B., Wexel, G., Tischer, T., Kruger, A., Plank, C., Anton, M., Martinek, V., Imhoff, A. B. and Gansbacher, B. (2008) Efficient and stable gene transfer of growth factors into chondrogenic cells and primary articular chondrocytes using a VSV.G pseudotyped retroviral vector. *Biomaterials* 29(9):1242-9.

Wilson S, Baird M, Ward V K. (2008) Delivery of vaccine peptides by rapid conjugation to baculovirus particles. *Vaccine* 26(20):2451-2456.

V Schirrmacher, C Haas, R Bonifer, T Ahlert, R Gerhards and C Ertel. (1999) Human tumor cell modification by virus infection: an efficient and safe way to produce cancer vaccine with pleiotropic immune stimulatory properties when using Newcastle disease virus. Gene Therapy 6(1): 63-73.

What is claimed is:

1. A method for inducing an immune response against a specific antigen in a mammalian subject in need thereof, comprising:
(a) transfecting into an insect cell a recombinant bacmid comprising (i) a nucleotide sequence encoding an envelope protein of an endogenous retrovirus; (ii) a first promoter that is operable in the insect cell and is operatively linked to (i); (iii) a nucleotide sequence encoding a second antigen protein not from any baculovirus and endogenous retrovirus; and (iv) a second promoter that is from a mammalian genome or virus, which is different the first promoter and is operatively linked to (iii); (b) obtaining a recombinant baculovirus vector produced from the insect cell, wherein the recombinant baculovirus vector is an endogenous retrovirus envelope-coated Baculovirus vector to express the second antigen; and (c) administering a pharmaceutically effective amount of the recombinant baculovirus of (b) to the mammalian subject.

2. The method according to claim 1, wherein the second antigen selected from group consisting of a viral antigen, a bacterial antigen, a parasitic antigen or a cancer antigen.

3. The method according to claim 2, wherein the second antigen comprises the viral antigen selected from the group consisting of HPV (human papillomavirus) antigen, HBV (hepatitis B virus) antigen, HCV (hepatitis C virus) antigen, HIV (human immunodeficiency virus) antigen, rotavirus antigen, influenza virus antigen, HSV (herpes simplex virus) antigen, avian influenza virus antigen, hog cholera virus antigen, foot-and-mouth disease virus antigen and Newcastle disease virus antigen.

4. The method according to claim 3, wherein the second antigen is HPV antigen, and the method is a method for preventing or treating a HPV infection-induced cancer.

5. The method according to claim 4, wherein the second antigen selected from group consisting of is HPV L1, L2, E6 or E7 protein.

6. The method according to claim 4, wherein the HPV antigen protein is selected from the group consisting of HPV type 1, 2, 3a, 4, 5, 6b, 7, 8, 9, 10, 11a, 12, 13, 16 and 18.

7. The method according to claim 1, wherein the endogenous retrovirus envelope protein is a HERV (human endogenous retrovirus) envelope protein.

8. The method according to claim 7, wherein the HERV envelope protein comprises the amino acid sequence of SEQ ID NO: 2.

9. The method according to claim 1, wherein the first promoter operable in the insect cell is selected from the group consisting of IE-1 promoter, IE-2 promoter, p35 promoter, p10 promoter, gp64 promoter and polyhedrin promoter.

10. The method according to claim 1, wherein the second promoter is selected from the group consisting of U6 promoter, H1 promoter, CMV (cytomegalo virus) promoter, adenovirus late promoter, vaccinia virus 7.5K promoter, SV40 promoter, HSV tk promoter, RSV promoter, human elongation factor 1α (hEF1α) promoter, methallothionein promoter, β-actin promoter, human IL-2 gene promoter, human IFN gene promoter, human IL-4 gene promoter, human lymphotoxin gene promoter, human GM-CSF gene promoter, TERT promoter, PSA promoter, PSMA promoter, CEA promoter, E2F promoter, AFP promoter and albumin promoter.

* * * * *

SEQUENCE LISTING

```
<160> NUMBER OF SEQ ID NOS: 10

<210> SEQ ID NO 1
<211> LENGTH: 1617
<212> TYPE: DNA
<213> ORGANISM: Artificial Sequence
<220> FEATURE:
<223> OTHER INFORMATION: Synthesized sequence of HERV envelope
<220> FEATURE:
<221> NAME/KEY: CDS
<222> LOCATION: (1)..(1614)

<400> SEQUENCE: 1 atg gcc ctg ccc tac cac att ttt ctg ttc acc gtg ctg ctg cct tcc      48
Met Ala Leu Pro Tyr His Ile Phe Leu Phe Thr Val Leu Leu Pro Ser
1               5                   10                  15 ttc acc ctg aca gcc cct cca cca tgc agg tgt atg aca tcc tcc tct      96
```

```
                Phe Thr Leu Thr Ala Pro Pro Pro Cys Arg Cys Met Thr Ser Ser
                                20                  25                  30 ccc tac cag gag ttt ctg tgg cgg atg cag aga ccc ggc aac atc gat        144
Pro Tyr Gln Glu Phe Leu Trp Arg Met Gln Arg Pro Gly Asn Ile Asp
             35                  40                  45 gcc cca agc tac cgg tcc ctg agc aaa ggc acc ccc acc ttc aca gcc        192
Ala Pro Ser Tyr Arg Ser Leu Ser Lys Gly Thr Pro Thr Phe Thr Ala
 50                  55                  60 cac aca cac atg ccc aga aac tgc tat cac tcc gcc acc ctg tgc atg        240
His Thr His Met Pro Arg Asn Cys Tyr His Ser Ala Thr Leu Cys Met
 65                  70                  75                  80 cac gcc aat acc cac tat tgg acc gga aaa atg att aat cct tct tgc        288
His Ala Asn Thr His Tyr Trp Thr Gly Lys Met Ile Asn Pro Ser Cys
                 85                  90                  95 cct ggc ggc ctg ggc gtg acc gtg tgc tgg aca tac ttt aca cag acc        336
Pro Gly Gly Leu Gly Val Thr Val Cys Trp Thr Tyr Phe Thr Gln Thr
            100                 105                 110 ggg atg agc gac ggc ggg ggc gtg cag gac cag gcc cgg gaa aag cac        384
Gly Met Ser Asp Gly Gly Gly Val Gln Asp Gln Ala Arg Glu Lys His
            115                 120                 125 gtg aaa gaa gtg atc agc cag ctg aca agg gtg cac gga aca agc tcc        432
Val Lys Glu Val Ile Ser Gln Leu Thr Arg Val His Gly Thr Ser Ser
130                 135                 140 cct tat aag gga ctg gac ctg tct aag ctg cac gag aca ctg cgg aca        480
Pro Tyr Lys Gly Leu Asp Leu Ser Lys Leu His Glu Thr Leu Arg Thr
145                 150                 155                 160 cac acc agg ctg gtg agc ctg ttc aac aca acc ctg aca ggc ctg cac        528
His Thr Arg Leu Val Ser Leu Phe Asn Thr Thr Leu Thr Gly Leu His
                165                 170                 175 gaa gtg tcc gcc cag aat cct acc aat tgt tgg atc tgc ctg cca ctg        576
Glu Val Ser Ala Gln Asn Pro Thr Asn Cys Trp Ile Cys Leu Pro Leu
            180                 185                 190 aat ttc cgg cct tac gtg tcc atc cct gtg ccc gag cag tgg aat aat        624
Asn Phe Arg Pro Tyr Val Ser Ile Pro Val Pro Glu Gln Trp Asn Asn
            195                 200                 205 ttc tct acc gaa atc aat acc acc tcc gtg ctg gtg ggc cca ctg gtg        672
Phe Ser Thr Glu Ile Asn Thr Thr Ser Val Leu Val Gly Pro Leu Val
210                 215                 220 tcc aac ctg gag att aca cac acc agc aat ctg acc tgt gtg aag ttt        720
Ser Asn Leu Glu Ile Thr His Thr Ser Asn Leu Thr Cys Val Lys Phe
225                 230                 235                 240 tcc aac acc aca tat acc acc aac agc cag tgc att agg tgg gtg acc        768
Ser Asn Thr Thr Tyr Thr Thr Asn Ser Gln Cys Ile Arg Trp Val Thr
                245                 250                 255 ccc ccc acc cag att gtg tgc ctg cca tct ggg atc ttc ttt gtg tgc        816
Pro Pro Thr Gln Ile Val Cys Leu Pro Ser Gly Ile Phe Phe Val Cys
            260                 265                 270 ggc aca agc gcc tac cgc tgt ctg aac ggg agc tcc gag agc atg tgc        864
Gly Thr Ser Ala Tyr Arg Cys Leu Asn Gly Ser Ser Glu Ser Met Cys
            275                 280                 285 ttt ctg agc ttc ctg gtg ccc cca atg acc atc tat aca gag cag gac        912
Phe Leu Ser Phe Leu Val Pro Pro Met Thr Ile Tyr Thr Glu Gln Asp
            290                 295                 300 ctg tat tct tac gtg atc tct aaa cca cgc aac aag cgg gtg cca att        960
Leu Tyr Ser Tyr Val Ile Ser Lys Pro Arg Asn Lys Arg Val Pro Ile
305                 310                 315                 320 ctg cca ttc gtg atc ggg gcc ggg gtg ctg ggc gcc ctg ggc acc ggg       1008
Leu Pro Phe Val Ile Gly Ala Gly Val Leu Gly Ala Leu Gly Thr Gly
                325                 330                 335
```

| | | | | | | | | | | | | | | | |
|---|---|---|---|---|---|---|---|---|---|---|---|---|---|---|---|
| atc | gga | ggc | atc | aca | act | agt | aca | cag | ttc | tac | tac | aaa | ctg | tct | cag |
| Ile | Gly | Gly | Ile | Thr | Thr | Ser | Thr | Gln | Phe | Tyr | Tyr | Lys | Leu | Ser | Gln |
| | | | 340 | | | | | 345 | | | | | 350 | | |

1056 gaa ctg aac ggc gac atg gag agg gtg gcc gat tct ctg gtg acc ctg   1104
Glu Leu Asn Gly Asp Met Glu Arg Val Ala Asp Ser Leu Val Thr Leu
            355                 360                 365 cag gac cag ctg aac tcc ctg gcc gcc gtg gtg ctg cag aat cgg agg   1152
Gln Asp Gln Leu Asn Ser Leu Ala Ala Val Val Leu Gln Asn Arg Arg
370                 375                 380 gcc ctg gat ctg ctg acc gcc gaa cgg ggc ggc acc tgt ctg ttt ctg   1200
Ala Leu Asp Leu Leu Thr Ala Glu Arg Gly Gly Thr Cys Leu Phe Leu
385                 390                 395                 400 ggg gag gaa tgc tgc tat tat gtg aac cag tcc gga atc gtg acc gag   1248
Gly Glu Glu Cys Cys Tyr Tyr Val Asn Gln Ser Gly Ile Val Thr Glu
                405                 410                 415 aag gtg aag gag atc cgc gac agg atc cag agg cgg gcc gaa gag ctg   1296
Lys Val Lys Glu Ile Arg Asp Arg Ile Gln Arg Arg Ala Glu Glu Leu
            420                 425                 430 aga aat acc ggc cca tgg ggc ctg ctg tct cag tgg atg ccc tgg att   1344
Arg Asn Thr Gly Pro Trp Gly Leu Leu Ser Gln Trp Met Pro Trp Ile
        435                 440                 445 ctg cca ttc ctg ggc ccc ctg gcc gcc att atc ctg ctg ctg ctg ttt   1392
Leu Pro Phe Leu Gly Pro Leu Ala Ala Ile Ile Leu Leu Leu Leu Phe
450                 455                 460 ggc ccc tgt atc ttc aac ctg ctg gtg aat ttc gtg tct agc aga atc   1440
Gly Pro Cys Ile Phe Asn Leu Leu Val Asn Phe Val Ser Ser Arg Ile
465                 470                 475                 480 gag gcc gtg aag ctg cag atg gag cct aag atg cag tcc aag aca aaa   1488
Glu Ala Val Lys Leu Gln Met Glu Pro Lys Met Gln Ser Lys Thr Lys
                485                 490                 495 atc tat cgc cgc cct ctg gac aga ccc gcc agc cct aga tct gac gtg   1536
Ile Tyr Arg Arg Pro Leu Asp Arg Pro Ala Ser Pro Arg Ser Asp Val
            500                 505                 510 aat gac att aag ggc acc cca cca gag gag atc tcc gcc gcc cag ccc   1584
Asn Asp Ile Lys Gly Thr Pro Pro Glu Glu Ile Ser Ala Ala Gln Pro
        515                 520                 525 ctg ctg agg ccc aac tct gcc ggg agc agc tga                       1617
Leu Leu Arg Pro Asn Ser Ala Gly Ser Ser
530                 535

<210> SEQ ID NO 2
<211> LENGTH: 538
<212> TYPE: PRT
<213> ORGANISM: Artificial Sequence
<220> FEATURE:
<223> OTHER INFORMATION: Synthetic Construct

<400> SEQUENCE: 2

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Ser Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

-continued

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Val Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
                180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
        210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
                260                 265                 270

Gly Thr Ser Ala Tyr Arg Cys Leu Asn Gly Ser Ser Glu Ser Met Cys
            275                 280                 285

Phe Leu Ser Phe Leu Val Pro Pro Met Thr Ile Tyr Thr Glu Gln Asp
        290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
                340                 345                 350

Glu Leu Asn Gly Asp Met Glu Arg Val Ala Asp Ser Leu Val Thr Leu
            355                 360                 365

Gln Asp Gln Leu Asn Ser Leu Ala Ala Val Val Leu Gln Asn Arg Arg
        370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
        450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
            515                 520                 525

Leu Leu Arg Pro Asn Ser Ala Gly Ser Ser
    530                 535

<210> SEQ ID NO 3
<211> LENGTH: 538
<212> TYPE: PRT
<213> ORGANISM: Artificial Sequence
<220> FEATURE:
<223> OTHER INFORMATION: Synthetic Construct

<400> SEQUENCE: 3

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
            35                  40                  45

Ala Pro Ser Tyr Arg Ser Leu Ser Lys Gly Thr Pro Thr Phe Thr Ala
        50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
            115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
                340                 345                 350

Glu Leu Asn Gly Asp Met Glu Arg Val Ala Asp Ser Leu Val Thr Leu
            355                 360                 365

Gln Asp Gln Leu Asn Ser Leu Ala Ala Val Val Leu Gln Asn Arg Arg
        370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535

<210> SEQ ID NO 4
<211> LENGTH: 1617
<212> TYPE: DNA
<213> ORGANISM: Human endogenous retrovirus

<400> SEQUENCE: 4
atggccctcc cttatcatat ttttctcttt actgttcttt taccctcttt cactctcact      60
gcaccccctc catgccgctg tatgaccagt agctcccctt accaagagtt ctatggaga     120 atgcagcgtc ccggaaatat tgatgcccca tcgtatagga gtctttctaa gggaaccccc    180
accttcactg cccacaccca tgcccccgc aactgctatc actctgccac tctttgcatg    240
catgcaaata ctcattattg acaggaaaa atgattaatc ctagttgtcc tggaggactt    300
ggagtcactg tctgttggac ttacttcacc caaactggta tgtctgatgg gggtggagtt    360
caagatcagg caagagaaaa acatgtaaaa gaagtaatct cccaactcac ccgggtacat    420
ggcacctcta gccctacaa aggactagat ctctcaaaac tacatgaaac cctccgtacc    480
catactcgcc tggtaagcct atttaatacc ccctcactg ggctccatga ggtctcggcc    540
caaaacccta ctaactgttg gatatgcctc ccctgaact tcaggccata tgtttcaatc    600
cctgtacctg aacaatggaa caacttcagc acagaaataa acaccacttc cgtttttagta    660 ggacctcttg tttccaatct ggaaataacc cataccctca acctcacctg tgtaaaattt    720
agcaatacta catacacaac caactcccaa tgcatcaggt gggtaactcc tcccacacaa    780
atagtctgcc taccctcagg aatatttttt gtctgtggta cctcagccta tcgttgtttg    840
aatggctctt cagaatctat gtgcttcctc tcattcttag tgcccccat gaccatctac    900 actgaacaag atttatacag ttatgtcata tctaagcccc gcaacaaaag agtacccatt    960

-continued

```
cttcctttg ttataggagc aggagtgcta ggtgcactag gtactggcat tggcggtatc    1020
acaacctcta ctcagttcta ctacaaacta tctcaagaac taaatgggga catggaacgg    1080
gtcgccgact ccctggtcac cttgcaagat caacttaact ccctagcagc agtagtcctt    1140
caaaatcgaa gagctttaga cttgctaacc gctgaaagag ggggaacctg tttatttta    1200 ggggaagaat gctgttatta tgttaatcaa tccggaatcg tcactgagaa agttaaagaa    1260
attcgagatc gaatacaacg tagagcagag gagcttcgaa acactggacc ctggggcctc    1320
ctcagccaat ggatgccctg gattctcccc ttcttaggac ctctagcagc tataatattg    1380
ctactcctct ttggaccctg tatctttaac ctccttgtta actttgtctc ttccagaatc    1440
gaagctgtaa aactacaaat ggagcccaag atgcagtcca agactaagat ctaccgcaga    1500
cccctggacc ggcctgctag cccacgatct gatgttaatg acatcaaagg caccctcct    1560 gaggaaatct cagctgcaca acctctacta cgccccaatt cagcaggaag cagttag      1617
```

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
ggctccggtg cccgtcagtg ggca                                           24

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
ttaattaacc cacgtttcaa catg                                           24

<210> SEQ ID NO 7
<211> LENGTH: 28
<212> TYPE: DNA
<213> ORGANISM: Artificial Sequence
<220> FEATURE:
<223> OTHER INFORMATION: Synthetic Construct

<400> SEQUENCE: 7
cagggccaca acaacggcat ctgctggg                                       28

<210> SEQ ID NO 8
<211> LENGTH: 28
<212> TYPE: DNA
<213> ORGANISM: Artificial Sequence
<220> FEATURE:
<223> OTHER INFORMATION: Synthetic Construct

<400> SEQUENCE: 8
ggctgcaggc cgaagttcca gtcctcca                                       28

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9

-continued

```
cagcgagacc acctacaaga                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gctgttcatg ctgtggatgt                                                    20
```